(12) United States Patent
Pirrung et al.

(10) Patent No.: US 6,225,625 B1
(45) Date of Patent: May 1, 2001

(54) SIGNAL DETECTION METHODS AND APPARATUS

(75) Inventors: Michael C. Pirrung, Durham, NC (US); J. Leighton Read; Stephen P. A. Fodor, both of Palo Alto, CA (US); Lubert Stryer, Stanford, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 08/456,598

(22) Filed: Jun. 1, 1995

Related U.S. Application Data

(62) Division of application No. 07/954,646, filed on Sep. 30, 1992, now Pat. No. 5,445,934, which is a division of application No. 07/850,356, filed on Mar. 12, 1992, now Pat. No. 5,405,783, which is a division of application No. 07/492,462, filed on Mar. 7, 1990, now Pat. No. 5,143,854, which is a continuation-in-part of application No. 07/362,901, filed on Jun. 7, 1989, now abandoned.

(51) Int. Cl.$^7$ .............................. G01N 1/161; F21V 9/16; C12Q 1/68; C07H 19/00
(52) U.S. Cl. ........................... 250/302; 250/458.1; 435/6; 435/7.1; 536/22.1; 536/25.32
(58) Field of Search ................................. 250/302, 458.1; 435/6, 7.1; 536/22.1, 25.32

(56) References Cited

U.S. PATENT DOCUMENTS

| | | | |
|---|---|---|---|
| 3,939,350 | * 2/1976 | Kronick et al. | 250/365 |
| 4,180,739 | 12/1979 | Abu-Shumays | 250/461 |
| 4,327,073 | 4/1982 | Huang | 424/1 |

(List continued on next page.)

FOREIGN PATENT DOCUMENTS

| | | |
|---|---|---|
| 0 063 810 | 11/1982 | (EP) . |
| 0 171 150 | 2/1986 | (EP) . |
| 0 173 339 | 3/1986 | (EP) . |

(List continued on next page.)

OTHER PUBLICATIONS

Ohtsuka et al. "Studies on transfer ribonucleic acids and related compounds. IX(1) Ribooligonucleotide synthesis using photosensitive o–nitrobenzyl protection at the 2'–hydroxyl group", Oct. 1974.*

Benschop et al., "Confocal compact scanning optical microscope based on compact disk technology," Abstract No. 114:256643p. Appl. Opt. 30(10):1179–1184, *Chemical Abstracts*, vol. 114(26) issued Jul. 1, 1991.*

Ekins et al., "Development of microspot multianalyte ratiometric immunoassay using dual fluorescent–labelled antibodies," *Analytica Chimica Acta* 227:73–96 (1989).*

Ekins et al., "Multianalyte microspot immunoassay—microanalytical 'compact disk' of the future," *Clin. Chem.*, 37(11):1955–1967 (1991).*

Quesada et al., "High–sensitivity DNA detection with a laser–excited confocal fluorescence gel scanner," *Biotechniques* 10:616–625 (1991).* van der Voort et al., "Design and use of a computer controlled confocal microscope for biological applications," *Scanning* 7:66–78 (1985).*

(List continued on next page.)

*Primary Examiner*—Jezia Riley
(74) *Attorney, Agent, or Firm*—Townsend and Townsend and Crew LLP

(57) ABSTRACT

A method and apparatus for preparation of a substrate containing a plurality of sequences. Photoremovable groups are attached to a surface of a substrate. Selected regions of the substrate are exposed to light so as to activate the selected areas. A monomer, also containing a photoremovable group, is provided to the substrate to bind at the selected areas. The process is repeated using a variety of monomers such as amino acids until sequences of a desired length are obtained. Detection methods and apparatus are also disclosed.

36 Claims, 20 Drawing Sheets

U.S. PATENT DOCUMENTS

| | | | |
|---|---|---|---|
| 4,342,905 | 8/1982 | Fujii et al. | 250/201 |
| 4,483,920 | 11/1984 | Gillespie et al. | 435/6 |
| 4,537,861 | 8/1985 | Elings et al. | 436/518 |
| 4,542,102 | 9/1985 | Dattagupta et al. | 435/6 |
| 4,562,157 | 12/1985 | Lowe et al. | 435/291 |
| 4,584,277 | 4/1986 | Ullman et al. | 436/501 |
| 4,613,566 | 9/1986 | Potter | 435/6 |
| 4,624,915 * | 11/1986 | Schindler et al. | 435/4 |
| 4,677,054 | 6/1987 | White et al. | 435/6 |
| 4,689,405 | 8/1987 | Frank | 536/27 |
| 4,704,353 | 11/1987 | Humphries et al. | 435/4 |
| 4,711,955 | 12/1987 | Ward et al. | 536/29 |
| 4,728,591 | 3/1988 | Clark et al. | 430/5 |
| 4,755,458 | 7/1988 | Rabbani et al. | 435/5 |
| 4,786,170 | 11/1988 | Groebler | 356/318 |
| 4,810,869 | 3/1989 | Yabe et al. | 250/201 |
| 4,820,630 | 4/1989 | Taub | 435/5 |
| 4,833,092 | 5/1989 | Geysen | 436/501 |
| 4,844,617 | 7/1989 | Kelderman et al. | 356/372 |
| 4,849,513 | 7/1989 | Smith et al. | 536/27 |
| 4,855,225 | 8/1989 | Fung et al. | 435/6 |
| 4,868,103 | 9/1989 | Stavrianopoulos et al. | 435/5 |
| 4,874,500 | 10/1989 | Madou et al. | 204/412 |
| 4,886,741 | 12/1989 | Schwartz | 435/5 |
| 4,888,278 | 12/1989 | Singer et al. | 435/6 |
| 4,923,901 | 5/1990 | Koester et al. | 521/53 |
| 4,925,785 | 5/1990 | Wang et al. | 435/6 |
| 4,981,783 | 1/1991 | Augenlicht et al. | 435/6 |
| 4,987,065 | 1/1991 | Stavrianopoulos et al. | 435/5 |
| 4,988,617 | 1/1991 | Landegren et al. | 435/6 |
| 4,994,373 | 2/1991 | Stavrianopoulos et al. | 435/6 |
| 5,002,867 | 3/1991 | Macevicz | 435/6 |
| 5,026,840 | 6/1991 | Dattagupta et al. | 536/27 |
| 5,028,525 | 7/1991 | Gray et al. | 435/6 |
| 5,043,265 | 8/1991 | Tanke et al. | 435/6 |
| 5,079,600 | 1/1992 | Schnur et al. | 357/4 |
| 5,082,830 | 1/1992 | Brakel et al. | 514/44 |
| 5,091,652 | 2/1992 | Mathies et al. | 250/458.1 |
| 5,143,854 | 9/1992 | Pirrung et al. | 436/518 |
| 5,192,980 | 3/1993 | Dixon | 356/326 |
| 5,200,051 * | 4/1993 | Cozzette et al. | 204/403 |
| 5,202,231 | 4/1993 | Drmanac et al. | 435/6 |
| 5,215,882 | 6/1993 | Bahl et al. | 435/6 |
| 5,232,829 | 8/1993 | Longiaru et al. | 435/6 |
| 5,310,893 | 5/1994 | Erlich et al. | 536/24 |
| 5,324,633 | 6/1994 | Fodor et al. | 435/6 |
| 5,348,855 | 9/1994 | Dattagupta et al. | 435/6 |
| 5,405,783 | 4/1995 | Pirrung et al. | 436/518 |
| 5,436,327 | 7/1995 | Southern et al. | 536/25.34 |
| 5,445,934 | 8/1995 | Fodor et al. | 435/6 |
| 5,447,841 | 9/1995 | Gray et al. | 435/6 |
| 5,486,452 | 1/1996 | Gordon et al. | 435/5 |
| 5,489,507 | 2/1996 | Chehab | 435/6 |
| 5,700,637 | 12/1997 | Southern | 435/6 |
| 6,054,270 | 4/2000 | Southern | 435/6 |

FOREIGN PATENT DOCUMENTS

| | | |
|---|---|---|
| 0 185 547 | 6/1986 | (EP). |
| 0 225 807 | 6/1987 | (EP). |
| 0 232 967 | 8/1987 | (EP). |
| 0 235 726 | 9/1987 | (EP). |
| 0 237 362 | 9/1987 | (EP). |
| 0 281 927 | 9/1988 | (EP). |
| 0 328 256 * | 8/1989 | (EP). |
| 0 337 498 | 10/1989 | (EP). |
| 0 392 546 | 10/1990 | (EP). |
| 0 333 561 | 9/1998 | (FR). |
| 2 156 074 | 10/1985 | (GB). |
| 63-223557 | 9/1989 | (JP). |
| WO84/03151 | 8/1984 | (WO). |
| WO85/01051 | 3/1985 | (WO). |
| WO88/04777 | 6/1988 | (WO). |
| WO89/08834 | 9/1989 | (WO). |
| WO89/11548 | 11/1989 | (WO). |
| WO 89/10977 * | 11/1989 | (WO) C12Q/1/68 |
| WO 90/03382 | 4/1990 | (WO) C07H/21/00 |
| WO90/04652 | 5/1990 | (WO). |
| WO 92/10092 | 6/1992 | (WO) A01N/1/02 |
| WO 93/02992 | 2/1993 | (WO) C07C/1/00 |

OTHER PUBLICATIONS

White et al., "An evaluation of confocal versus conventional imaging of biological structures by fluorescence light microscopy," *J. of Cell Biology* 105:41–48 (1987).*

Yamamoto et al., "Features and applications of the laser scanning microscope," *J. of Modern Optics* 37:1691–1701 (1990).*

Bannwarth et al., "Laboratory Methods: A System for the Simultaneous Chemical Synthesis of Different DNA Fragments on Solid Support," *DNA,* 5(5):413–419 (1986).

Bannwarth, W., "Gene Technology: a Challenge for a Chemist," *CHIMIA,* 41(9):302–317 (1987).

Haridasan et al., "Peptide Synthesis Using Photolytically Cleavable 2–Nitrobenzyloxycarbonyl Protecting Group," *Proc. Indian Natl. Sci. Acad.,* Part A (1987) 53:717–728.

Sze/McGillis, *VLSI Technology,* Chapter 7, pp. 267–301, McGraw–Hill, 1983.

Geysen et al., "Strategies for epitope analysis using peptide synthesis," J. Immunol. Meth. (1987) 102:259–274.

Furka et al., "More Peptides by Less Labor," Abstract No. 288 from Xth International Symposium on Medicinal Chemistry, Budapest, Hungary, Aug. 15–19, 1988.

Kleinfeld et al., "Controlled Outgrowth of Dissociated Neurons on Patterned Substrates," *J. of Neurosci.* (1988) 8:4098–4120.

BioRad, *Chromatography, Electrophoresis, Immunochemistry, Molecular Biology, HPLC,* Catalogue M 1987, pp. 182.

Hames & Higgins (ed.), *Nucleic Acid Hybridizaiton: A Practical Approach* (1985) IRL Press, Oxford, England.

Barinaga, "Will 'DNA Chip' Speed Genome Initiative?" *Science* (1991) 253:1489.

Khrapko et al., "An Oligonucleotide hybridization approach to DNA sequencing," *FEBS* (1989) 256:118–122.

Mirzabekov, "DNA sequencing by hybridization—a megasequencing method and a diagnostic tool?" *TIBTECH* (1994) 12:27–32.

Southern et al., "Analyzing and Comparing Nucleic Acid Sequences by Hybridization to Arrays of Oligonucleotides: Evaluation Using Experimental Models," *Genomics* (1992) 13:1008–1017.

van der Voort et al., "Design and use of a computer controlled confocal microscope for biological applications," *Scanning* 7:66–78 (1985).

Urdea et al., "A Novel Method For The Rapid Detection of Specific Nucleotide Sequence in Crude Biological Samples Without Blotting or Radioactivity; Application to the Analysis of Hepatitis B Virus In Human Serum," Gene 61, 253–264 (1987).

Frank, et al., "Simultaneous Synthesis and Biological Applications of DNA Fragments: An Efficient and Complete Methodology," Methods in Enzymology, 154:221–251 (1987).

Augenlicht, et al., "Cloning and Screening of Sequences Expressed in a Mouse Colon Tumor," Cancer Research, 42,1088–1093.

Masiakowski, et al., "Cloning of cDNA sequences of hormone–regulated genes from the MCF–7 human breast cancer cell line," Nucleic Acids Research, 10:7895–7903 (1982).

Bartsh et al., "Cloning of mRNA sequences from the human colon: Preliminary characterization of defined mRNAs in normal neoplastic tissues," Br. J. Cancer, 54:791–798 (1986).

Hasse et al "Detection of two Viral Genomes in Single Cells by Double–Label Hybridization in Situ and Color Microradioautography," Science 227, 189–192 (1985).

Lanier, et al, "Human Lymphocyte Subpopulations Identified by Using Three–Color Immunofluorescence and Flow Cytometry Analysis", The Journal of Immunology, 132:151–156 (1984).

Wallace et al., "Hybridization of synthetic oligodeoxyribonucleotides to *x 174 DNA: the effect of single base pair mismatch", Nucleic Acids Research, 11:3543–3577 (1979).

Lasky, et al., "Messenger RNA prevalence in sea urchin embryos measured with cloned cDNAs," Proc. Natl. Acad. Sci. USA, 77:5317–5321 (1986).

Hanahan et al., "Plasmid screening at high colony density", Gene 10:63–67 (1980).

Hanahan et al., "Plasmid screening at high density," Methods in Enzymology, 100:333–342 (1983).

Love, et al., "Screening of Lambda Library for Differentially Expressed Genes Using in Vitro Transcripts," Anal Biochem, 150:429–41 (1985).

Wu, et al., "Synthesis and Properties of Adnosine–5'–triphosphoro–y–1–(5–sulfonic acid) naphthyl Ethylamidate: A Fluorescent Nucleotide Substrate for DNA–Dependent RNA Polymerase from Escherichia coli" Arch Biochem Biophys, 246:564–71 (1989).

Yarbrough, et al., "Synthesis and Properties of Flourescent Nucleotide Substrates for DNA–dependent RNA Polymerases," J. Biol. Chem. 254:12069–73 (1979).

Titus, et al., "Texas Red, A Hydrophilic, Red–Emitting Fluorophore for use with Fluorescein in Dual Parameter Flow Microfluorometric and Fluorescence Microscopic Studies," Journal of Immunological Methods, 50:193–204. (1982).

*Loken, et al, "Three–Color Immunofluorescence Analysis of Leu Antigens on Human Peripheral Blood Using Two Lasers on a Fluorescence–Activated Cell Sorter," Cymoetry 5:151–158 (1984).

Sim, et al., "Use of a cDNA Library for Studies on Evolution and Developmental Expression of the Chorion Multigene Families", Cell 18:1303–1316 (1979).

Augenlicht et al., "Expression of Cloned Sequences in Biopsies of Human Colonic Tissue and in Colonic Carcinoma Cells Induced to Differentiate in Vitro," Cancer Research, 47, 6017–6021 (1987).

Urdea et al., "A comparison of non–radioisotopic hybridization assay methods using fluorescent, chemiluminescent and enzyme labeled synthetic oligodeoxyribonucleotide probes," Nucleic Acids Research, 16: 4937–4956 (1988).

Lysov et al., "A New Method For Determining the DNA Nucleotide Sequence by Hybridization with Olgonucleotides," Doklady Biochemistry, 303:436–438 (1989).

Khrapko et al., "An Oligonucleotide Hybridization Approach to DNA Sequencing," FEBS Letters, 256:118–122 (1989).

*Hopman et al., "Bi–color detection of two target DNAs by non–radioactive in situ hybridization," Histochemistry, 85:1–4 (1986).

Widacki et al., "Biochemical Differences in Qa–2 Antigens Expressed By Qa–2+,6+ and Qa–2+,6– Strains. Evidence for Differential Expression of the Q7 and Q9 Genes," Molecular Immunology, 27:559–570 (1990).

Tkachuk et al., "Detection of bcr–abl Fusion in Chronic Myelogenous Leukemia by in situ Hybridization," Science, 250:559–562 (1990).

*Chehab et al., "Detection of specific DNA sequences by fluorescence amplification: A color complementation assay," Proceedings of the national Academy of Sciences, 86:9178–9182 (1989).

Lu et al., "Differential screening of murine ascites cDNA libraries by means of in vitro transcripts of cell–cycle–phase–specific cDNA and digital image processing," Gene, 86:185–192 (1990).

Tsusumi et al., "Expression of L– and M–Type Pyruvate Kinase in Human Tissues," Genomics, 2:86–89 (1988).

Saiki et al., "Genetic analysis of amplified DNA with immobilized sequence–specific oligonucleotide probes," Proceedings of the national Academy of Sciences, 86:6230–6234 (1989).

Bains and Smith, A Novel Method for Nucleic Acid Sequence Determination. Theor. Biol. 135: 303–307 (1988).

Boyle et al, Differential distribution of long and short interspersed element sequences in the mouse genome: Chromosome karyotyping by fluorescence in situ hybridization, J. Proc. Natl. Acad. Sci. USA 87:7757–7761 (1990).

*Carrano et al, A High–Resolution. Fluorescence–Based. Semiautomated Method for DNA Fingerprinting, Genomics 4, 129–136 (1989).

Caruthers, Gene Synthesis Machines: DNA Chemistry and Its Uses, Science 230: 281 (1985).

*Chehab et al, Detection of sickle cell anemia mutation by colour DNA Amplification, The Lancet 335:15–17 (1990).

Craig et al, Ordering of Cosmid Clones Covering the Herpes Simplex Virus Type I (HSV–I) Genome, Nuc. Acids. Res. 18:2653–2660 (1990).

Drmanac et al, Laboratory Methods—Reliable Hybridization of Oligonucleotides as Short as Six Nucleotides, DNA and Cell Biology, 9:527–534 (1990).

* Ekins et al, Fluorescence Spectroscopy and its Application to a New Generation of High Sensitivity, Multi–Microspot. Multianalyte, Immunoassay, Clinica Chimica Acta 194:91–114 (1990).

Gergen et al, Filter Replicas and Permanent Collections of Recombinant DNA Plasmids, Nucliec Acids Res. 7:2115–2135 (1979).

Kerkof & Kelly, A Procedure for Making Simultaneous Determinations of the Relative Levels of Gene transcripts in Tissues or Cells, Anal. Biochem., 188: 349–355 (1990).

Kimura et al, An Immobilized Enzyme Membrane Fabrication Method Using an Ink Jet Nozzle, Biosensors 40:41–52 (1988).

Kleinfeld et al, Controlled Outgrowth of Dissociated Neurons on Patterned Substrates. J. Neuroscience 8:4098–4120 (1988).

Kohara et al, The Physical Map of the Whole *E. coli* Chromosome: Application of a New Strategy for Rapid Analysis and Sorting of a large Genomic Library, *Cell* 50: 495–508 (1987).

Lichter, Ward, et al, Rapid detection of human chromosome 21 aberrations by in situ hybridization, *Proc. Natl. Acad. Sci. USA* 85:9664–9668 (1988).

Lichter et al, Fluorescence in situ hybridization with Alu and L1 polymerase chain reaction probes for rapid characterization of human chromosomes in hybrid cell lines, *Proc. Natl. Acad. Sci. USA* 87:6634–6638 (1990).

*Lichter et al, High–Resolution Mapping of Human Chromosome 11 by in Situ Hybridization with Cosmid Clones, *Science* 247 (1990).

* Lichter & Ward, Is non–isotopic in situ hybridization finally coming of age? *Nature,* 345: 93–94 (1990).

Scharf et al., "HLA class II allelic variation and susceptibility to pemphigus vulgaris," Proceedings of the National Academy of Sciences, 85:3504–3508 (1988).

*Kitazawa, et al. "In situ DNA–RNA hybridiazation using in vivo bromodeoxyuridine–labeled DNA probe," Histochemistry, 92:195–199 (1989).

*Fan et al., "Mapping small DNA sequences by fluorescence in situ hybridization directly on banded metaphase chromosomes," Proceedings of the national Academy of Sciences, 87:6223–6227 (1990).

Michiels et al., "Molecular approaches to genome analysis: a strategy for the construction of ordered overlapping clone libraries" CABIOS 3(3):203–210 (1987).

Poustka, et al., "Molecular Approaches to Mammalian Genetics", Cold Spring Harbor Symp. Quant. Biol., (1986).

Nederlof et al., "Multiple Fluorescence In Situ Hybridization," Cytometry, 11:126–131 (1990).

Drmanac et al., "Partial Sequencing by Oligo–Hybridization: Concept and Applications in Genome Analysis," The First International Conference on Electrophoresis, Supercomputing and the Human Genome 60–74 (1990).

Evans et al., "Physical mapping of complex genomes by cosmid multiplex analysis," Proceedings of the national Academy of Sciences, 86:5030–5034 (1989).

* Brock, et al., "Rapid fluorescence detection of in situ hybridization with biotinylated bovine herpesvirus–1 DNA probes," Journal of Veterinary Diagnostic Investigation, 1:34–38 (1989).

Lysov, "DNA Sequencing By Oligonucleotide Hybridization," in The First Intl. Conf. Electrophoresis. Supercomputing and the Human Genome. Eds. Cantor and Lim, *World Scientific,* pp. 157–163. (Apr. 1990).

Nakamori et al, A Simple and Useful Method for Simultaneous Screening of Elevated Levels of Expression of a Variety of Oncogenes in Malignant Cells, *Jpn. J. Cancer Res.* (Gann), 79:1311–1317 (1988).

Sambrook et al, *"Molecular Cloning—A Laboratory Manual—Second Edition"* vols. 1–3, Cold Spring Harbor Laboratory Press (1989).

Turchinskii et al, Multiple Hybridization in Genome Analysis. The Reaction of Diamines and Bisulfite with Cytosine for Introduction of Nonradioactive Labels into DNA. *Molekulyarnaya Biologiya* (English Translation), 22: 1229–1235 (1988).

* Kievits et al., "Rapid subchromosomal localization of cosmids by nonradioactive in situ hybridization," Cytogenetics and Cell Genetics, 53:134–136 (1990).

Gummerlock, et al., "RAS Enzyme–Linked Immunoblot Assay Discrimintates p21 Species: A Technique to Dissect Gene Family Expression," Analytical Biochemistry, 180:158–168 (1989).

Drmanac et al., "Sequencing by Oligonucleotide Hybridization: A Promising Framework in Decoding of the Genome Program," The First International Conference on Electrophoresis, Supercomputing and the Human Genome 60–74 (1990).

Drmanac et al., "Sequencing of Megabase Plus DNA by Hybridization: Theory of the Method," Genomics, 4:114–128 (1989).

Young, "Simultaneous Use of Digoxigenin– and Radiolabeled Oligodeoxyribonucleotide Probes for Hybridization Histochemistry," Neuropeptides, 13:271–275 (1989).

Ezaki et al., "Small–Scale DNA Preparation for Rapid Genetic Identification of Campylobacter Species without Radioisotope," Microbiology Immunology, vol. 32 (2), 141–150 (1988).

Morrison et al., "Solution–Phase Detection of Polynucleotides Using Interacting Flourescent Labels and Competitive Hybridization," Analytical Biochemistry, 183:231–244 (1989).

Meinkoth & Wahl, Hybridization of Nucleic Acids Immobilized on Solid Supports, , *Analytical Biochemistry* 138, 267–284 (1984).

Wu et al, Direct Analysis of Single Nucleotide Variation in Human DNA and RNA Using In Situ Dot Hybridization, *DNA* 8:135–142 (1989).

* cited by examiner

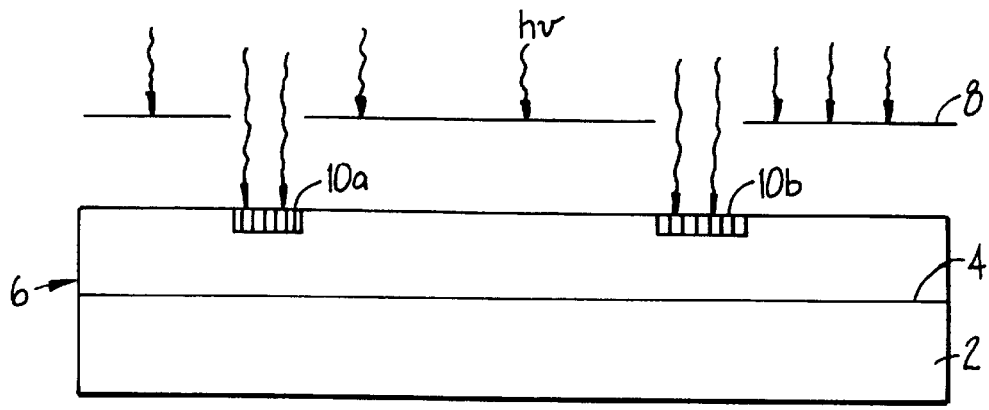
FIG._1.
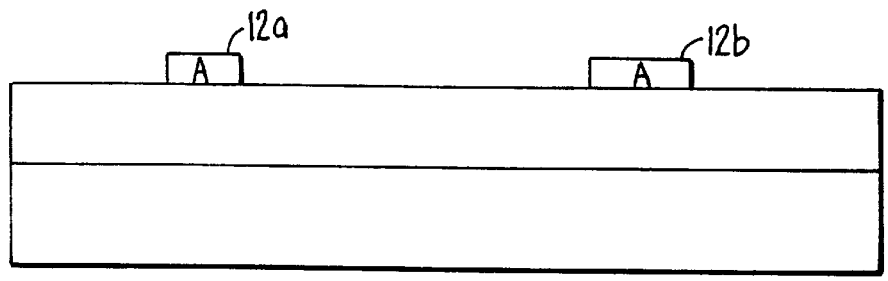
FIG._2.
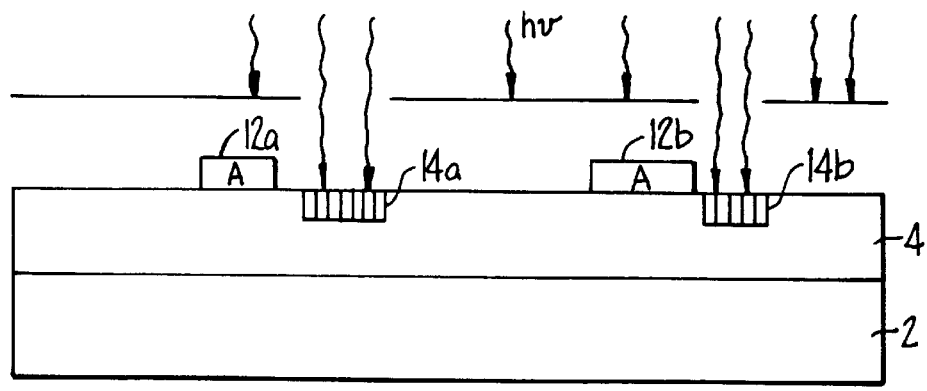
FIG._3.
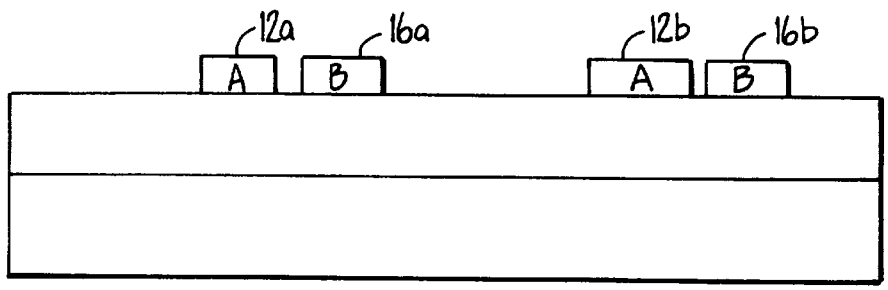
FIG._4.

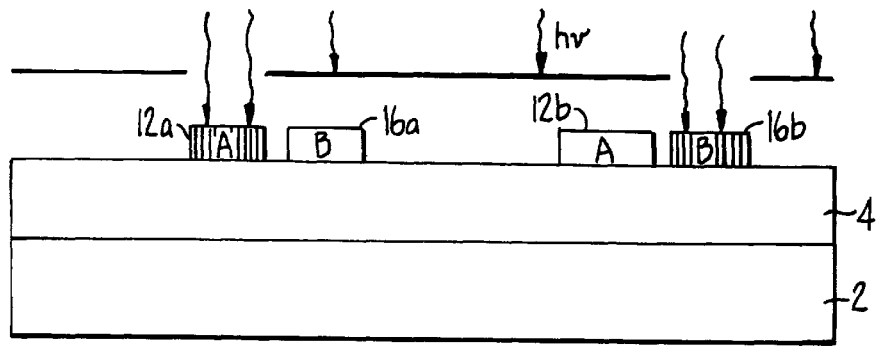
FIG._5.
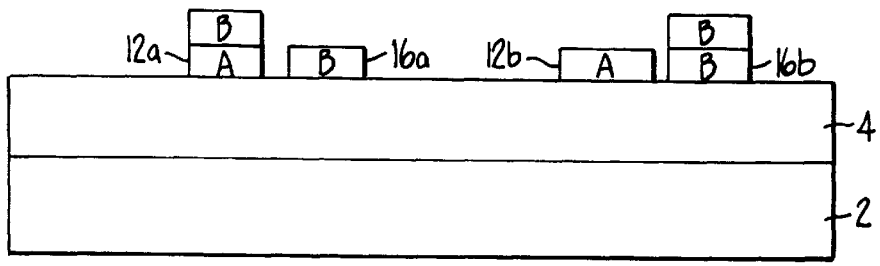
FIG._6.
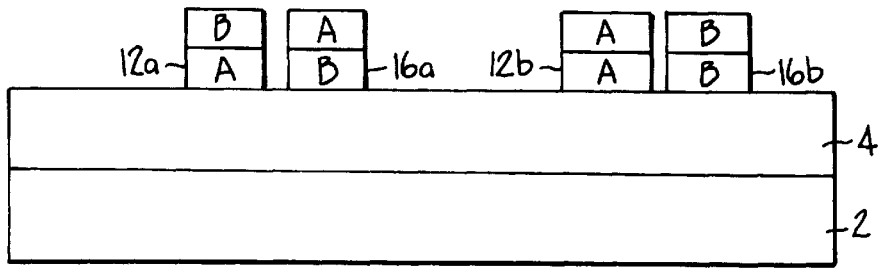
FIG._7.
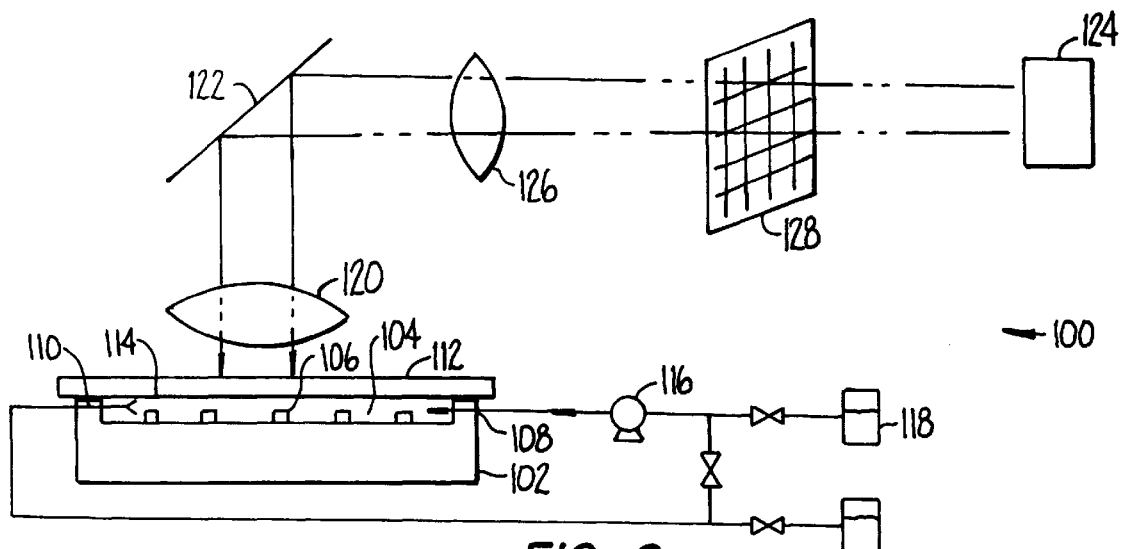
FIG._8a.

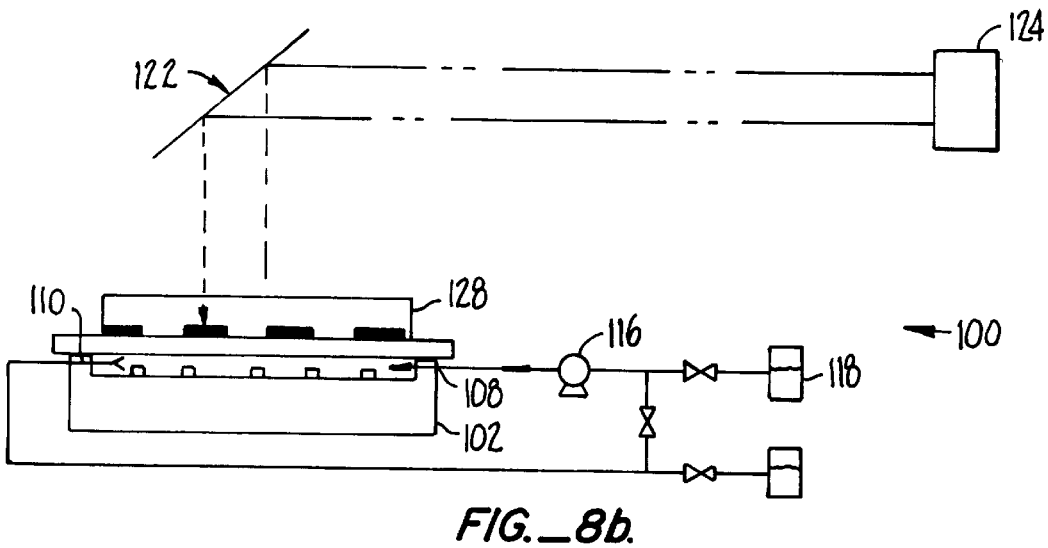
FIG._8b.
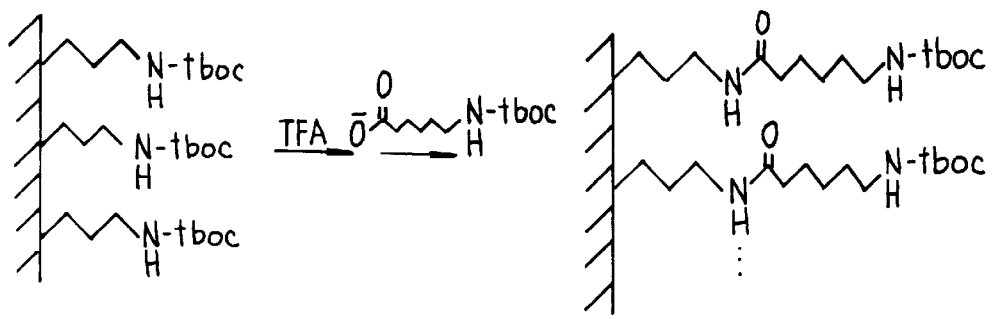
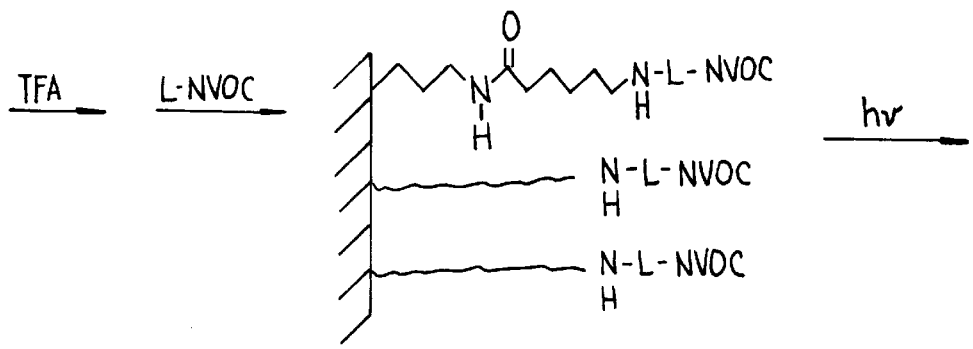
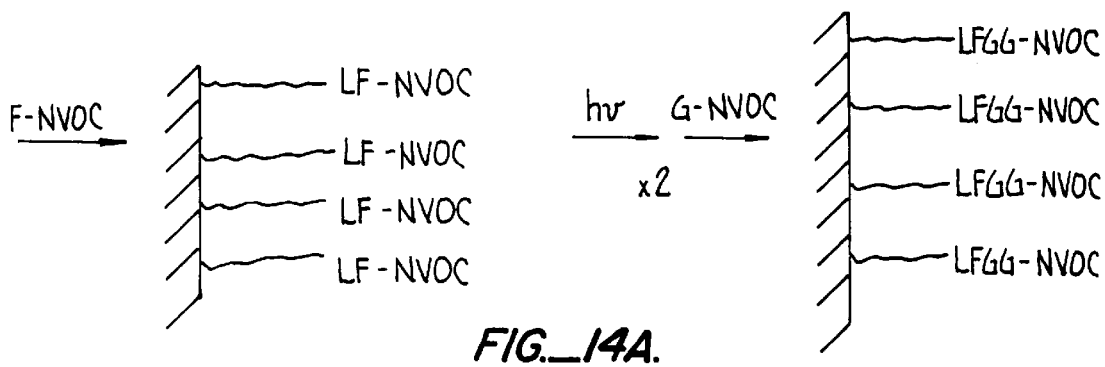
FIG._14A.

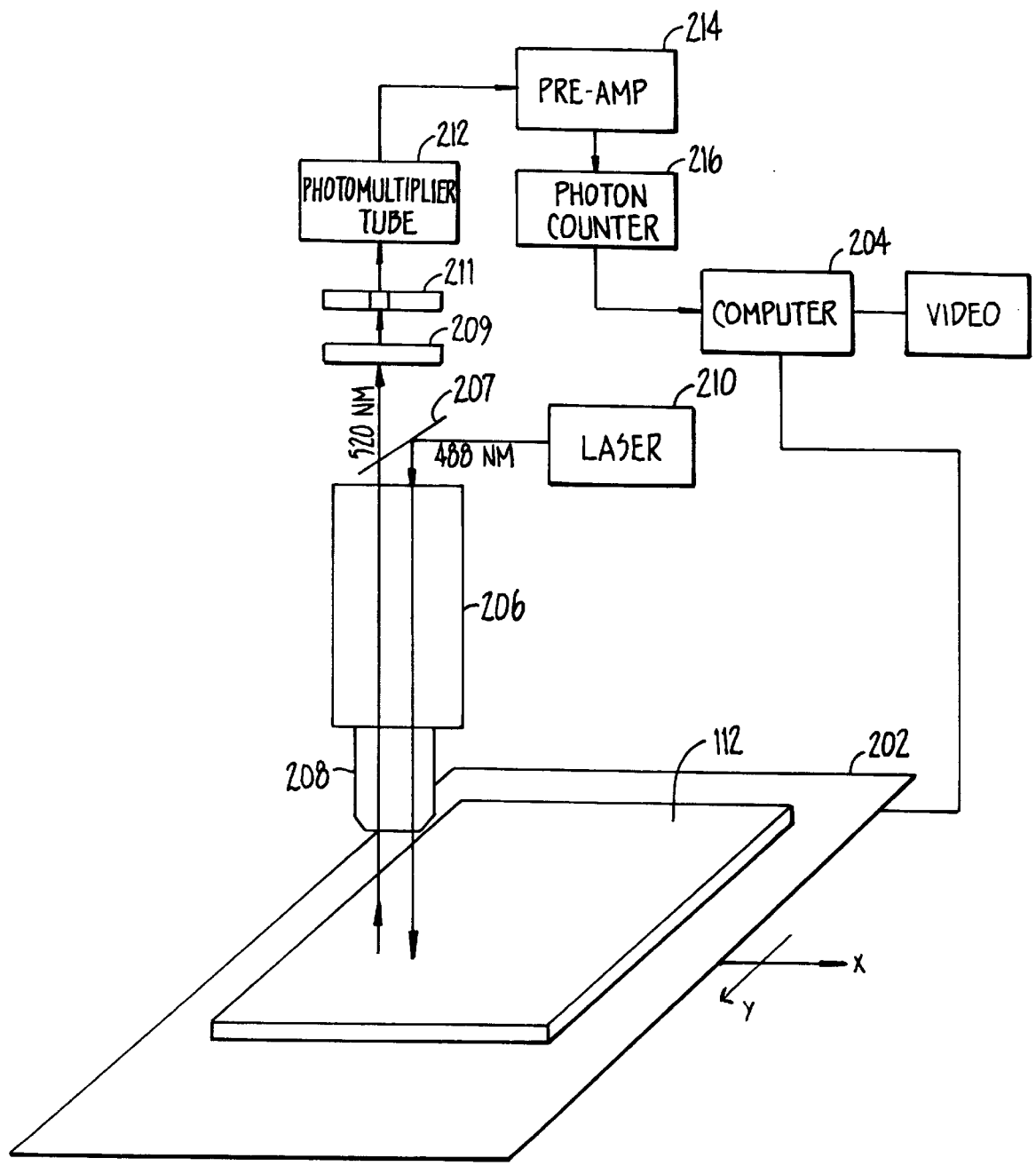
FIG._9.

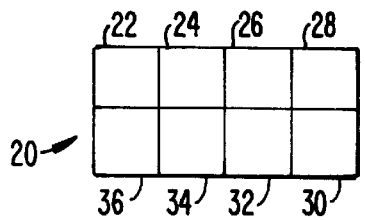
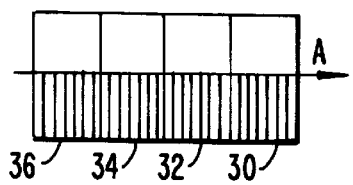
FIG._10A.  FIG._10B.
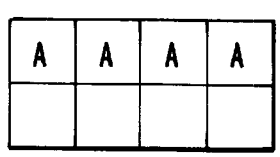
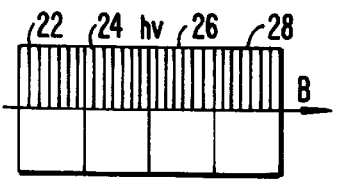
FIG._10C.  FIG._10D.
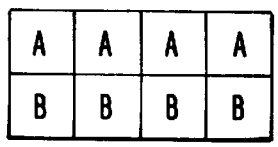
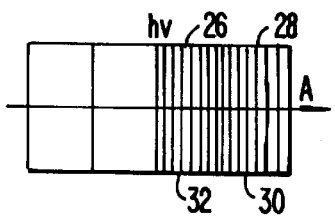
FIG._10E.  FIG._10F.
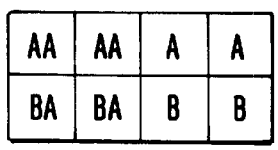
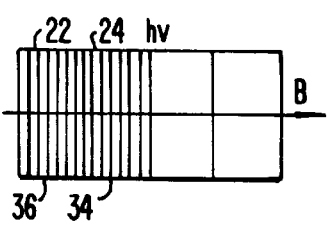
FIG._10G.  FIG._10H.
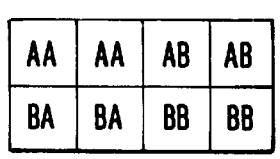
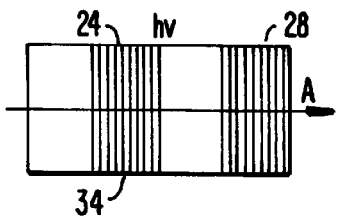
FIG._10I.  FIG._10J.
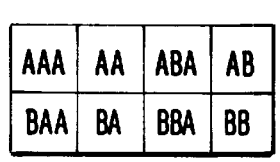
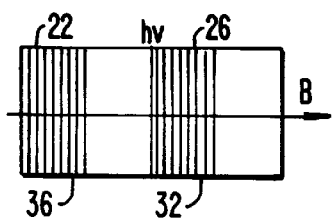
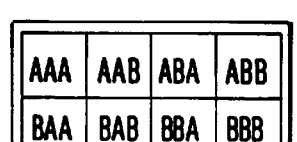
FIG._10K.  FIG._10L.  FIG._10M.

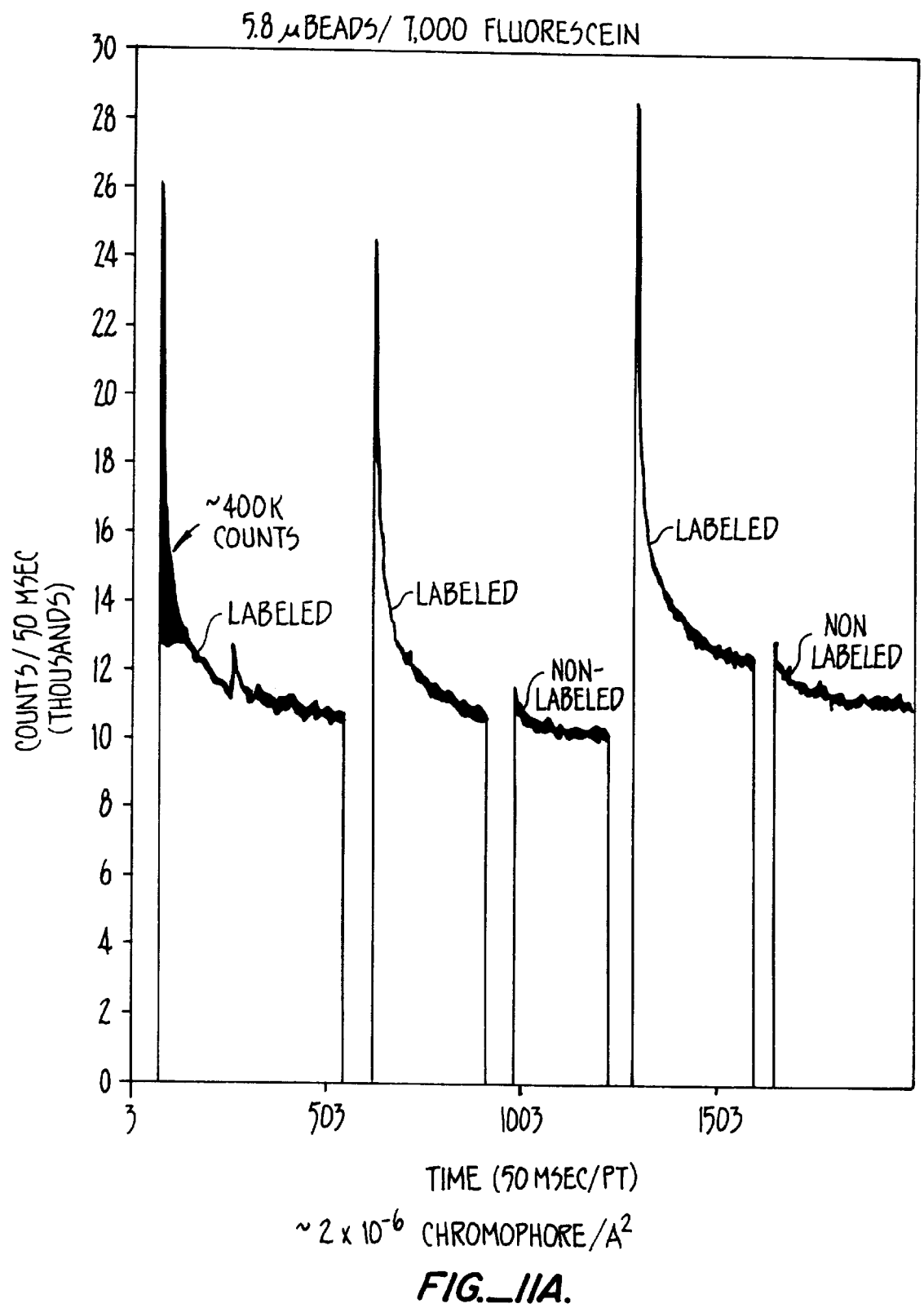
FIG._11A.

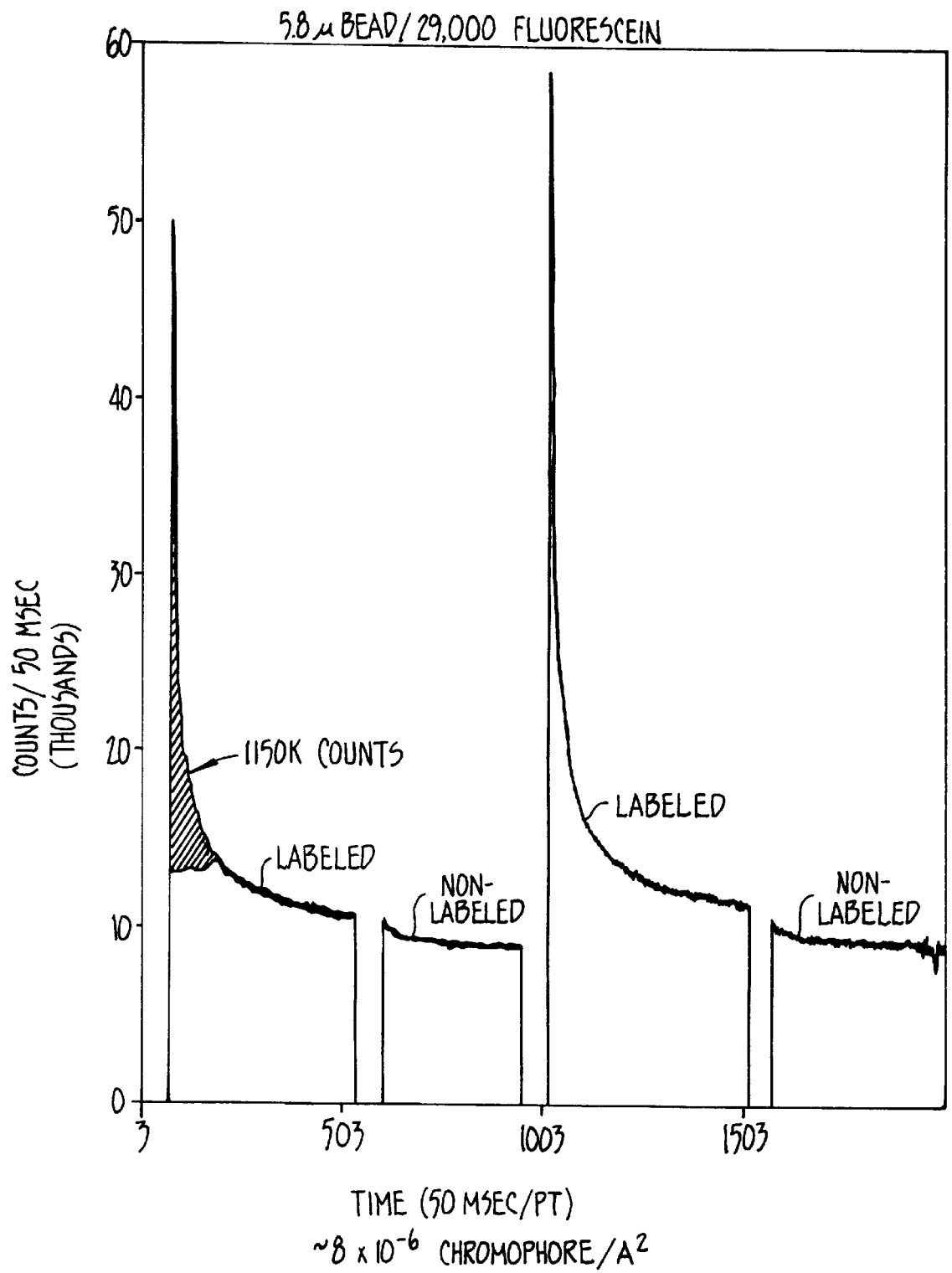
FIG._11B.

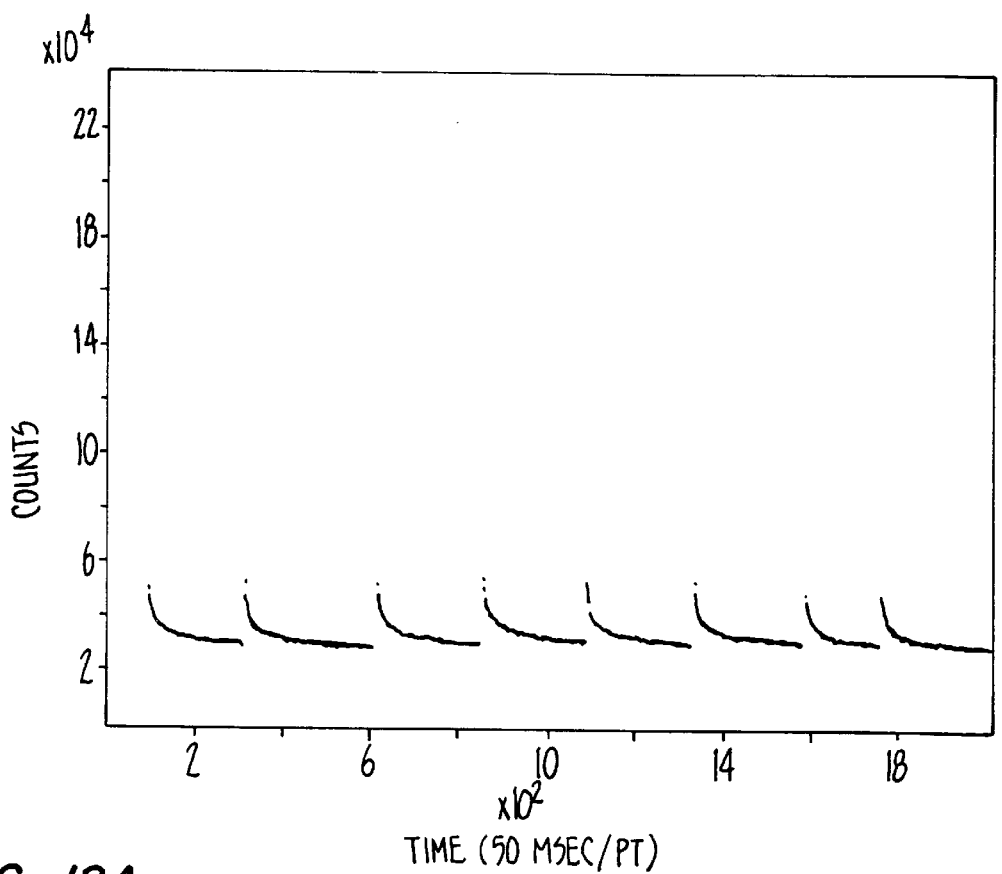
FIG._12A.
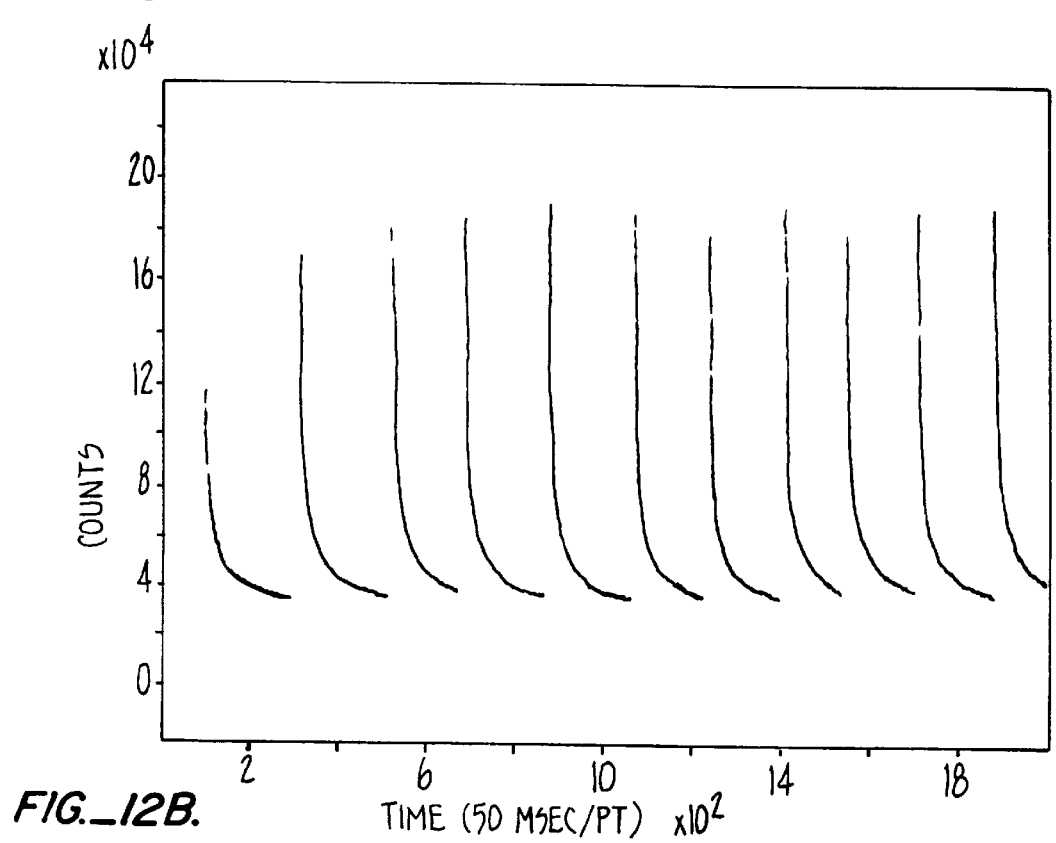
FIG._12B.

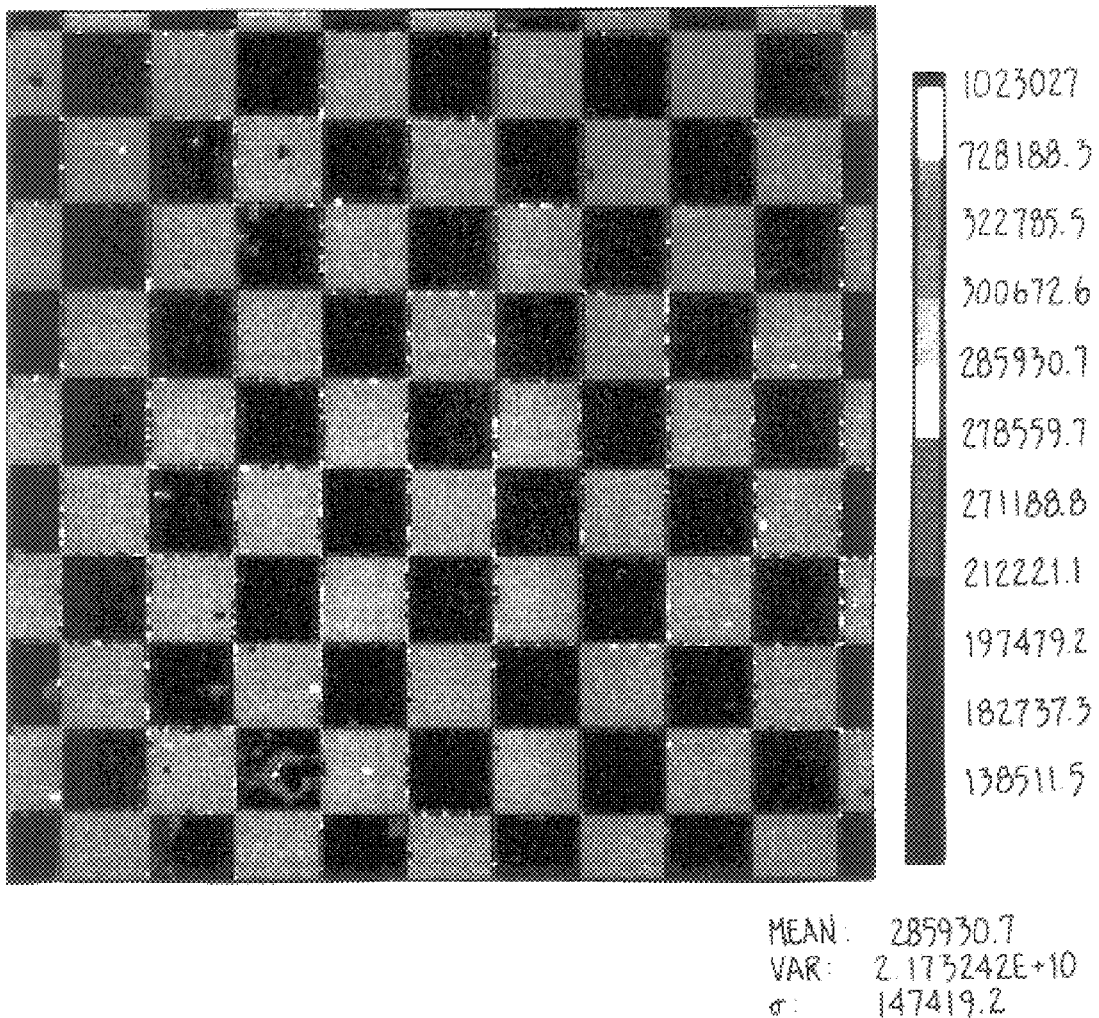
FIG._13A.

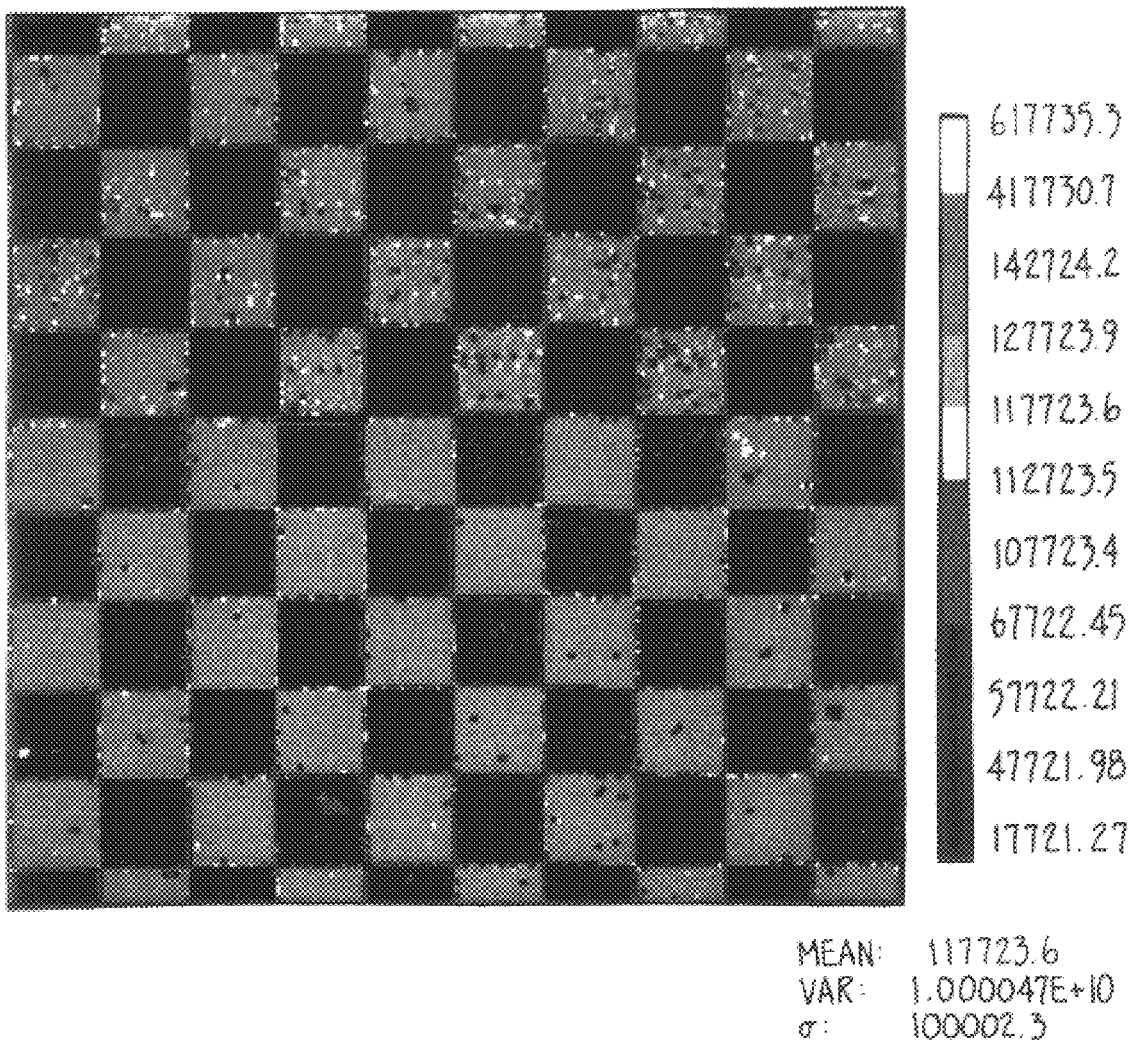
FIG._13B.

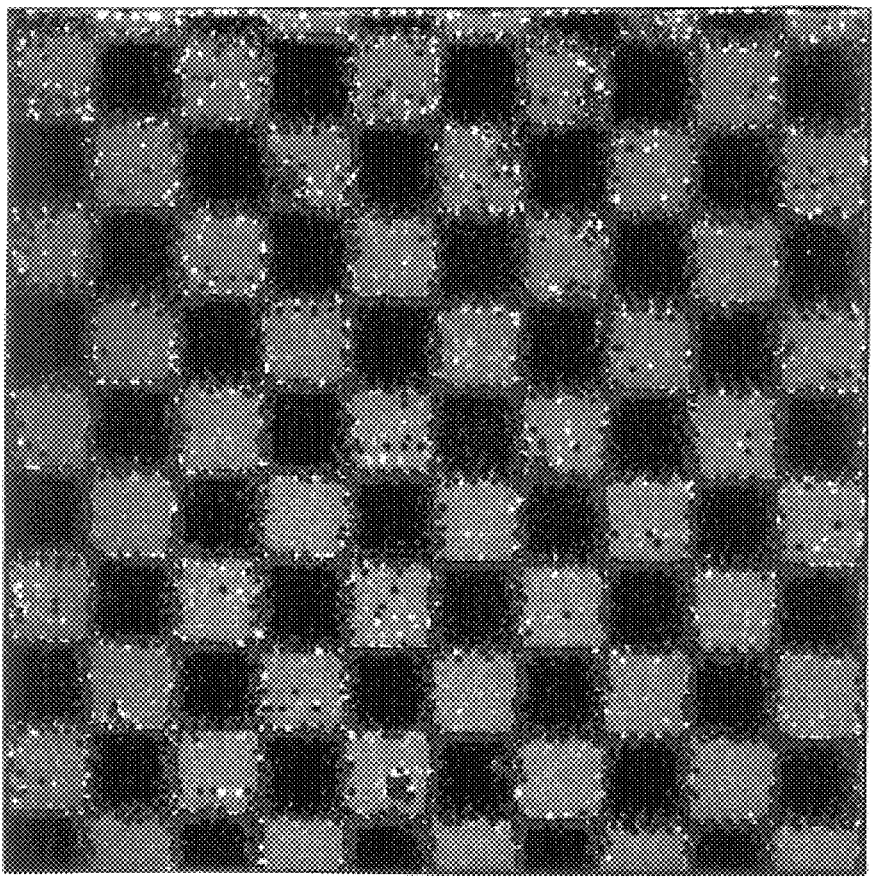
FIG._13C.

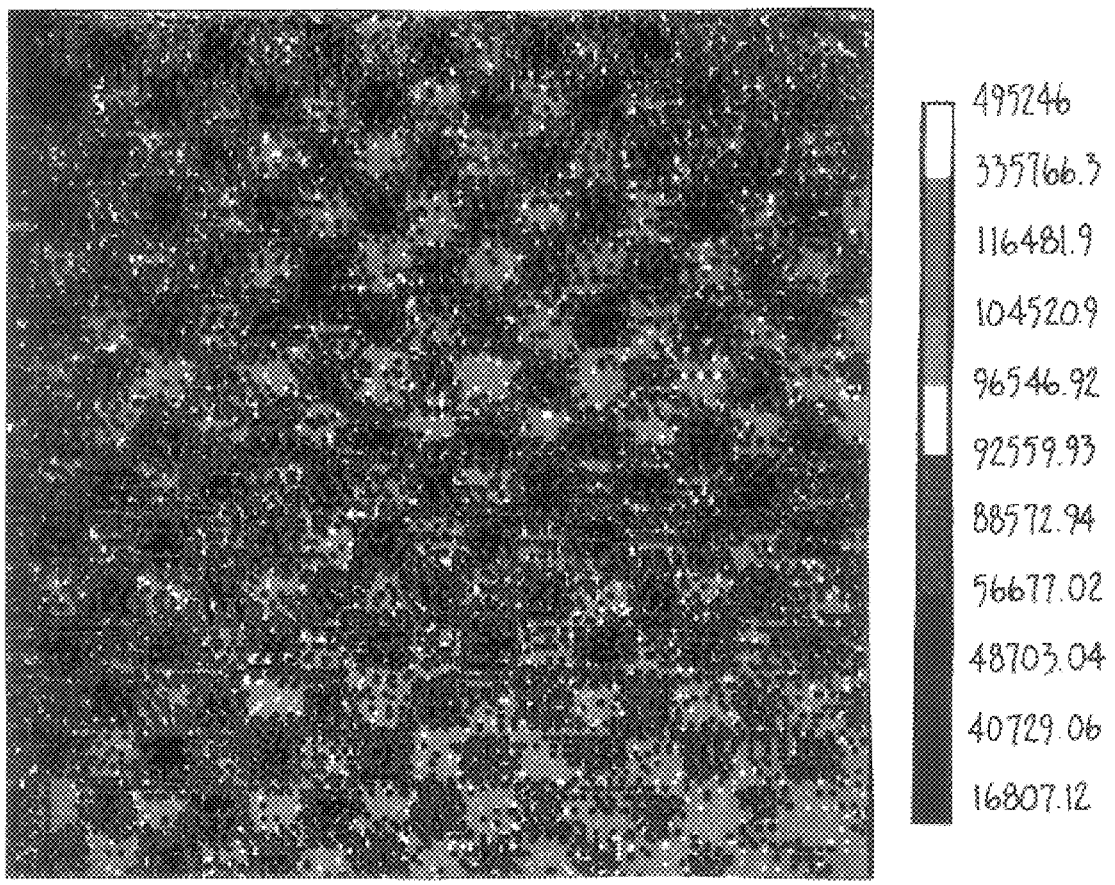
FIG._13D.

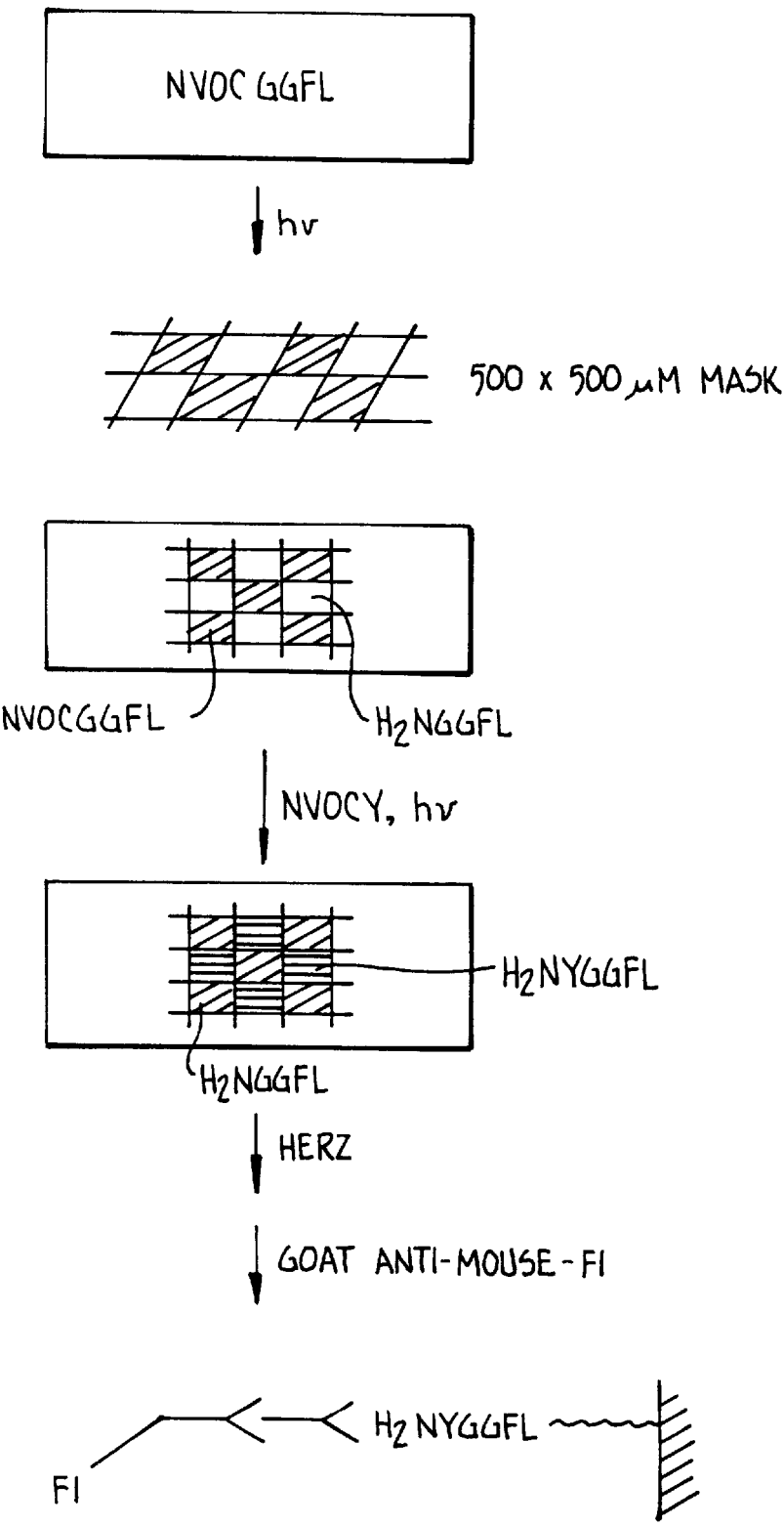
FIG._14B.

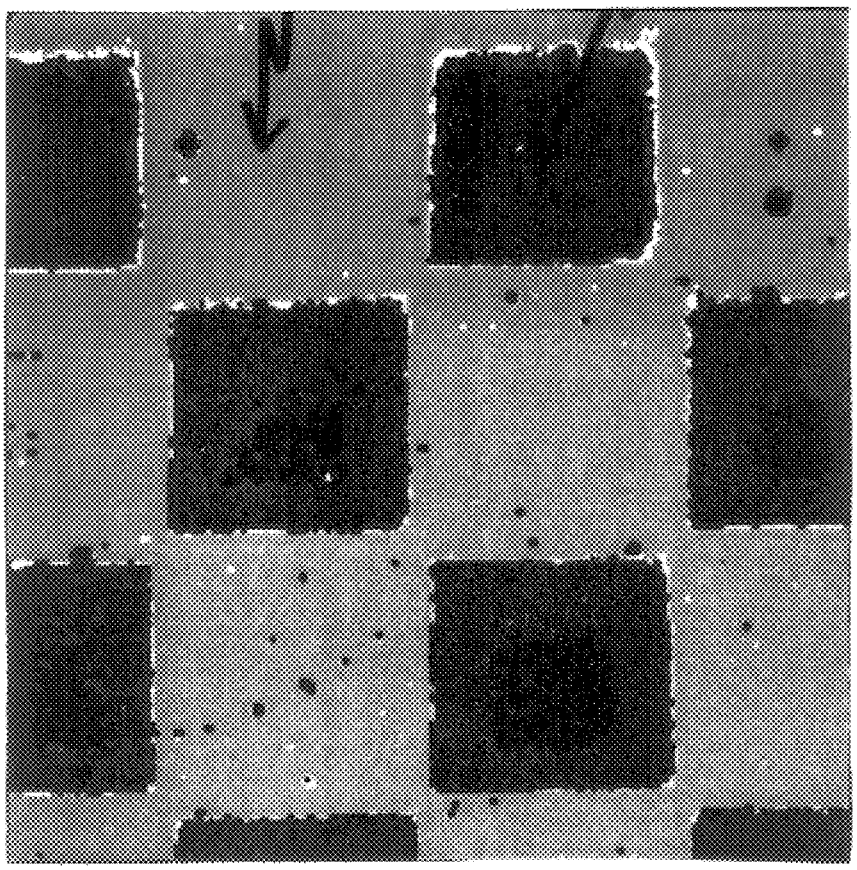
FIG._15A.

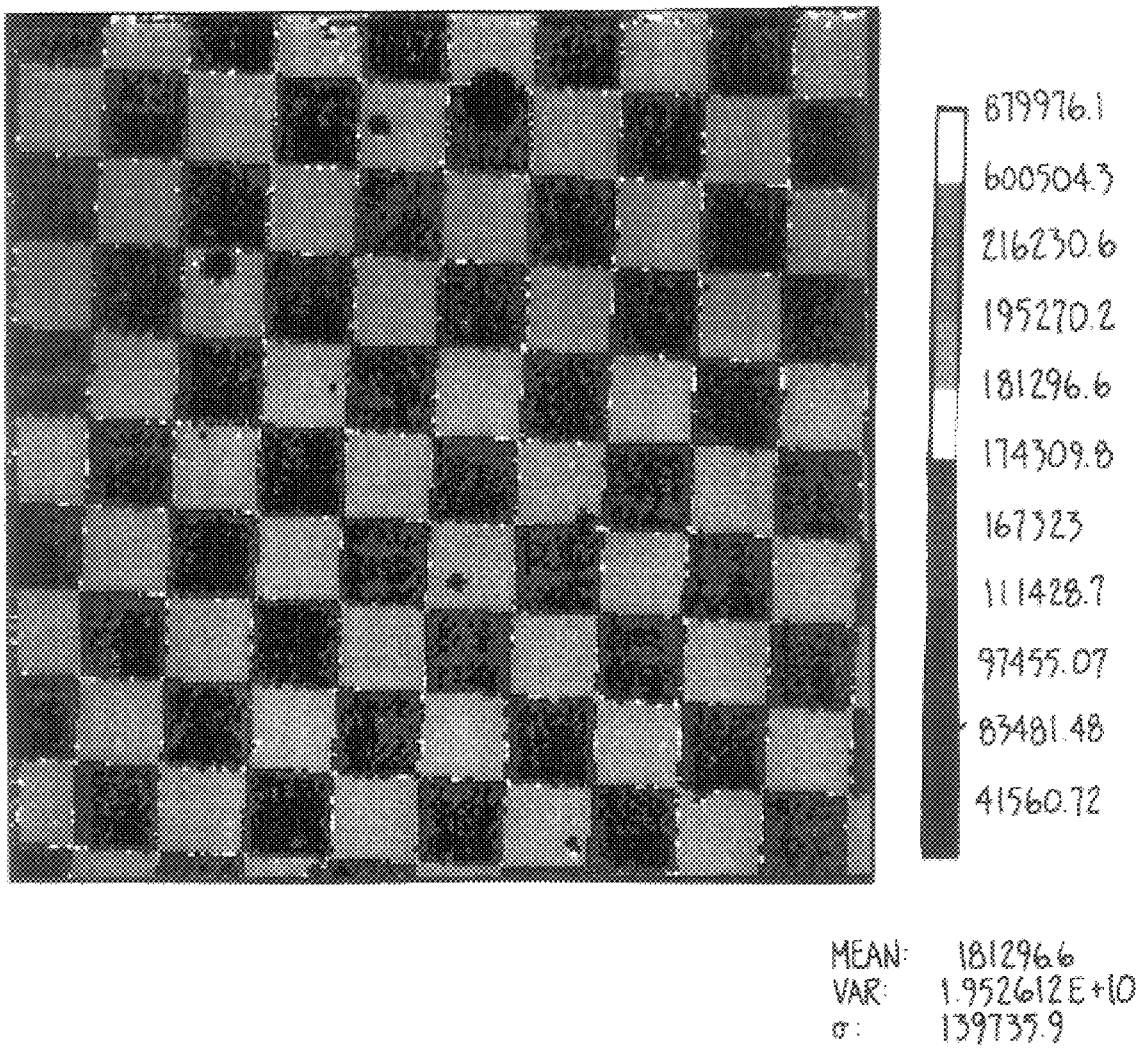
FIG._15B.

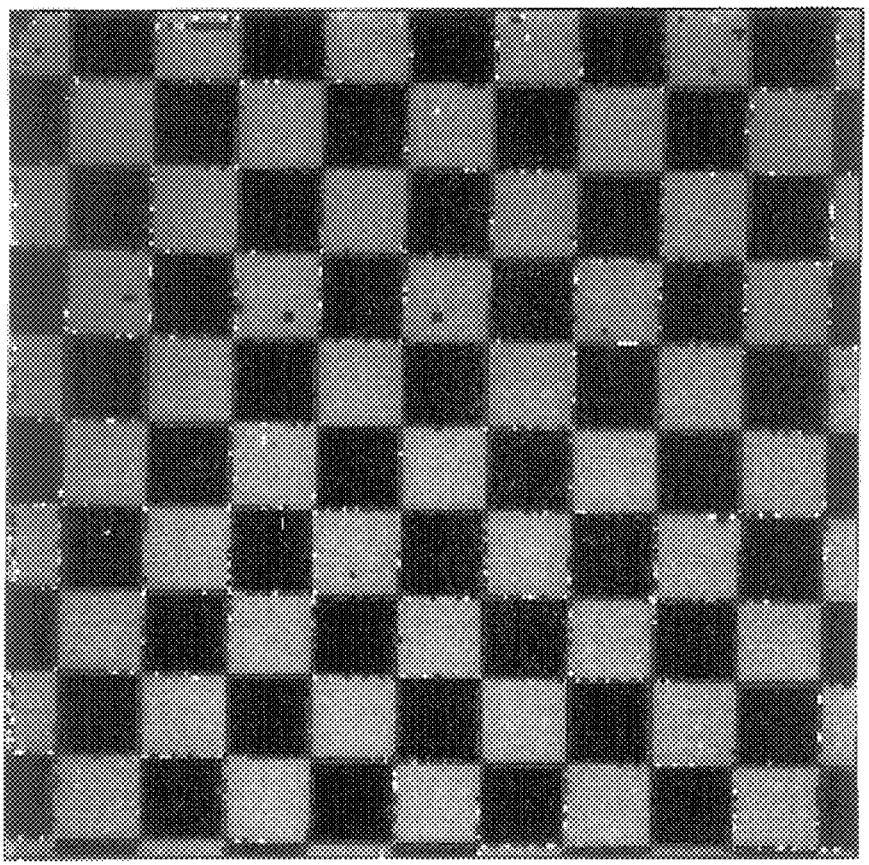
FIG._16.

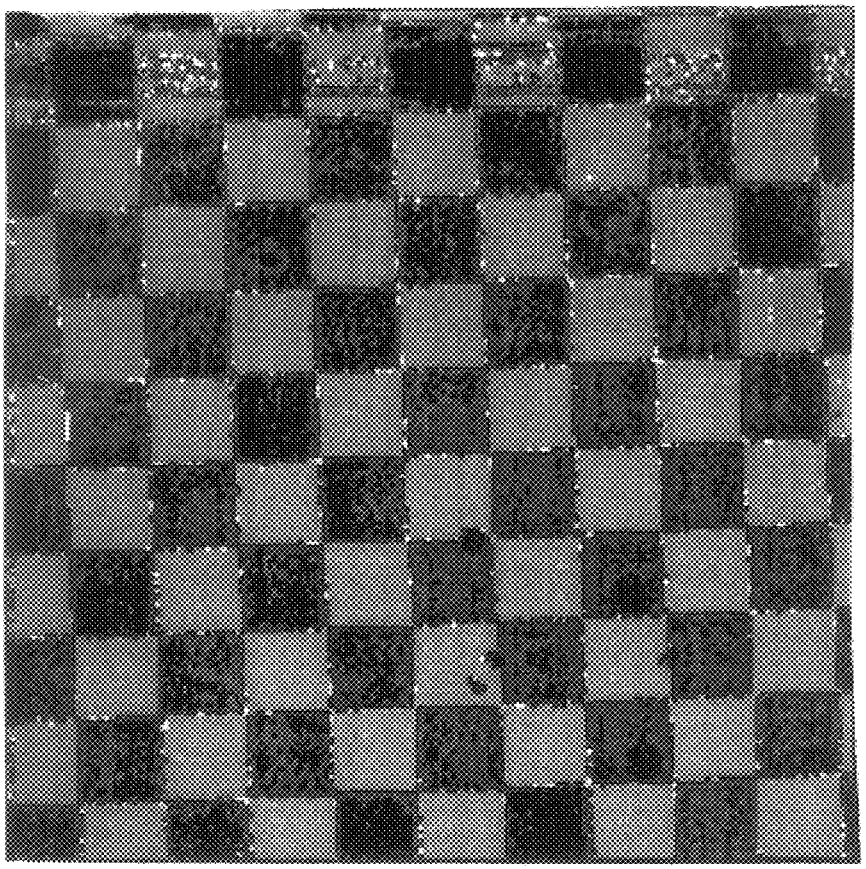
FIG._17.

|  | P | A | S | G |  |
|---|---|---|---|---|---|
| L | LPGFL | LAGFL | LSGFL | LGGFL | L |
|  | FPGFL | FAGFL | FSGFL | FGGFL | F |
|  | WPGFL | WAGFL | WSGFL | WGGFL | W |
|  | YPGFL | YAGFL | YSGFL | YGGFL | Y |

L SET

FIG._18A.

|  | p | a | s | G |  |
|---|---|---|---|---|---|
|  | YpGFL | YaGFL | YsGFL | YGGFL | Y |
|  | fpGFL | faGFL | fsGFL | fGGFL | f |
|  | wpGFL | waGFL | wsGFL | wGGFL | w |
|  | ypGFL | yaGFL | ysGFL | yGGFL | y |

D SET

FIG._18B.

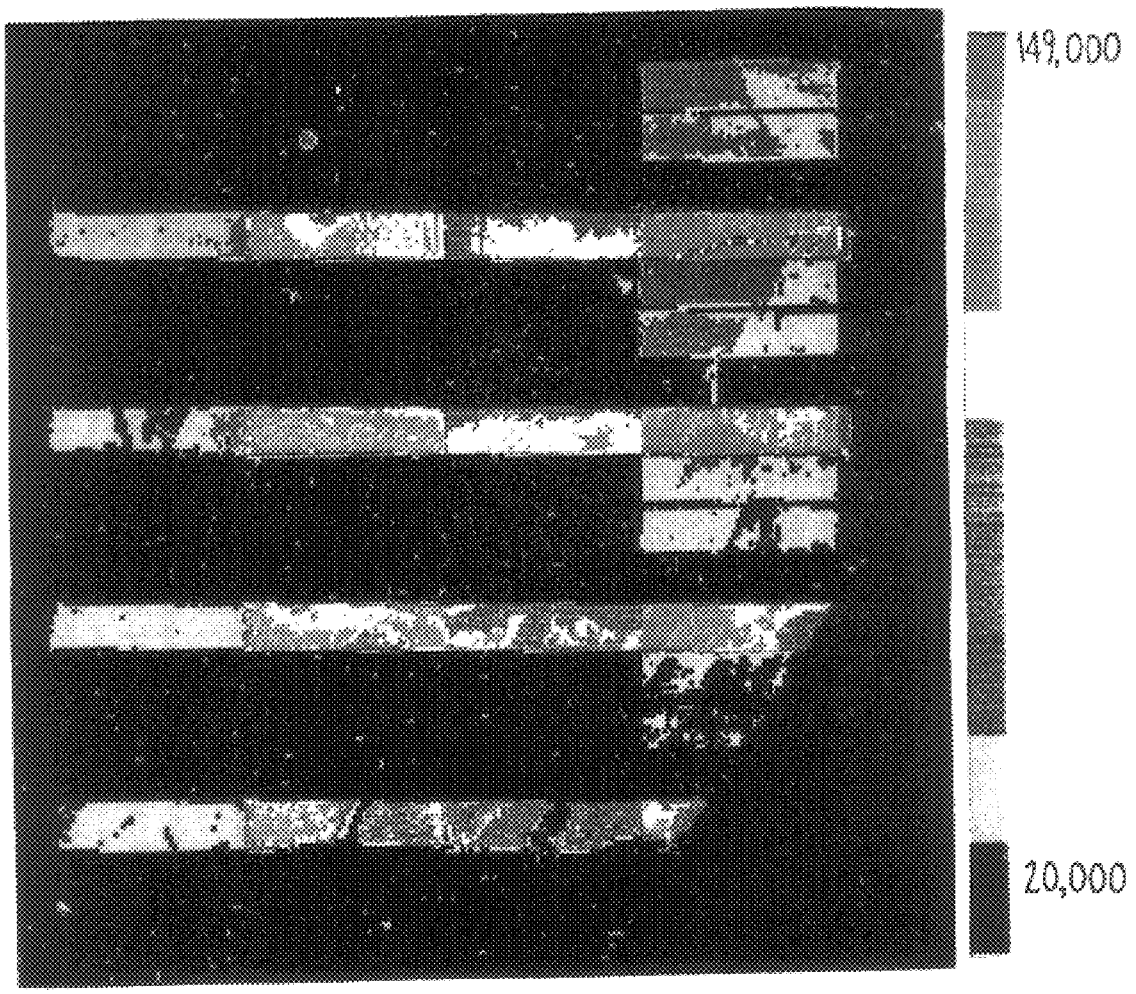
FIG._19.

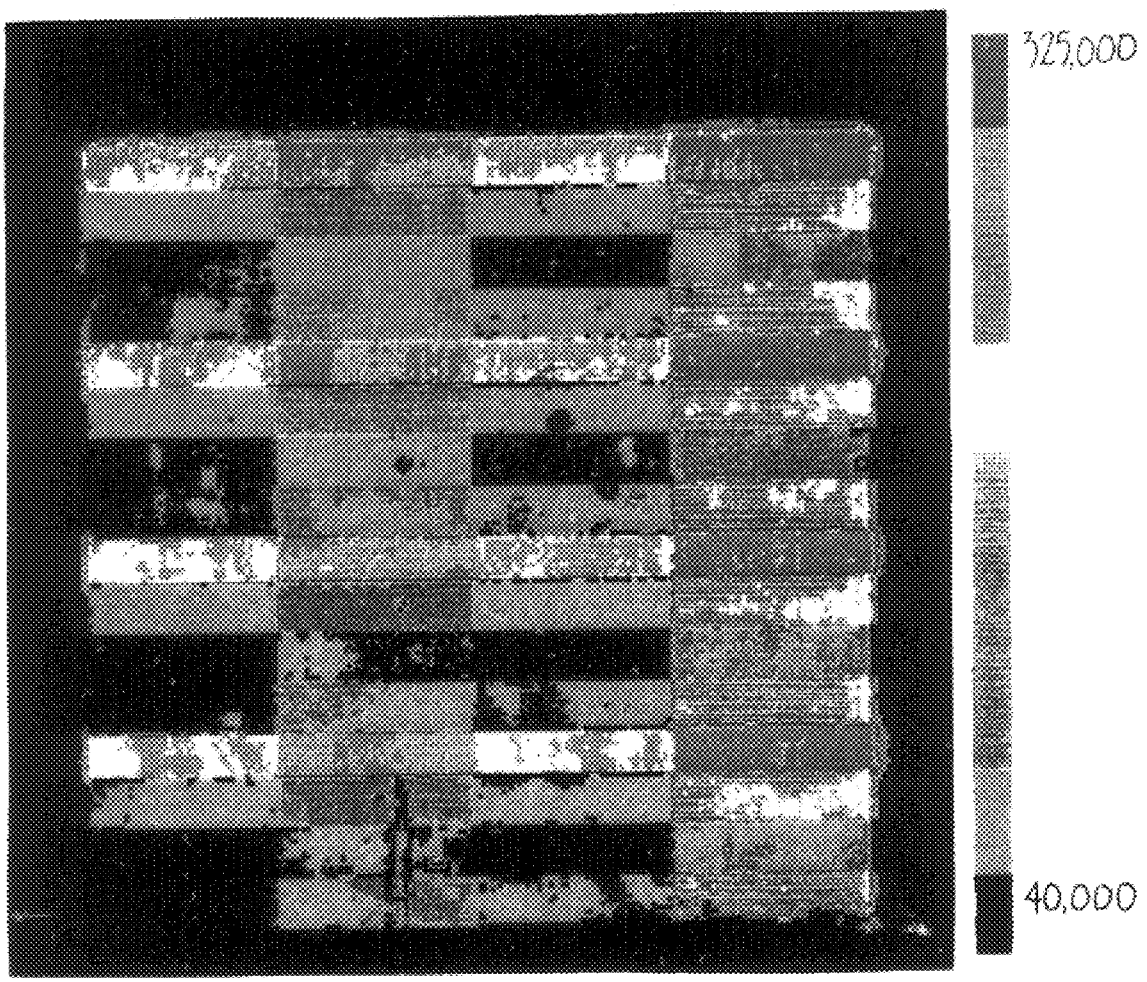
FIG._20.

SIGNAL DETECTION METHODS AND APPARATUS

CROSS-REFERENCE TO RELATED APPLICATIONS

This application is a Rule 60 Division of U.S. Ser. No. 07/954,646, filed Sep. 30, 1992, now U.S. Pat. No. 5,445,934, which is a Rule 60 Division of U.S. Ser. No. 07/850,356, filed Mar. 12, 1992, now U.S. Pat. No. 5,405,783, which is a Rule 60 Division of U.S. Ser. No. 07/492,462, filed Mar. 7, 1990, now U.S. Pat. No. 5,143,854, which is a Continuation-in-Part of U.S. application Ser. No. 07/362,901, filed Jun. 7, 1989, now abandoned, and assigned to the assignee of the present invention.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

The present inventions relate to the synthesis and placement of materials at known locations. In particular, one embodiment of the inventions provides a method and associated apparatus for preparing diverse chemical sequences at known locations on a single substrate surface. The inventions may be applied, for example, in the field of preparation of oligomer, peptide, nucleic acid, oligosaccharide, phospholipid, polymer, or drug congener preparation, especially to create sources of chemical diversity for use in screening for biological activity.

The relationship between structure and activity of molecules is a fundamental issue in the study of biological systems. Structure-activity relationships are important in understanding, for example, the function of enzymes, the ways in which cells communicate with each other, as well as cellular control and feedback systems.

Certain macromolecules are known to interact and bind to other molecules having a very specific three-dimensional spatial and electronic distribution. Any large molecule having such specificity can be considered a receptor, whether it is an enzyme catalyzing hydrolysis of a metabolic intermediate, a cell-surface protein mediating membrane transport of ions, a glycoprotein serving to identify a particular cell to its neighbors, an IgG-class antibody circulating in the plasma, an oligonucleotide sequence of DNA in the nucleus, or the like. The various molecules which receptors selectively bind are known as ligands.

Many assays are available for measuring the binding affinity of known receptors and ligands, but the information which can be gained from such experiments is often limited by the number and type of ligands which are available. Novel ligands are sometimes discovered by chance or by application of new techniques for the elucidation of molecular structure, including x-ray crystallographic analysis and recombinant genetic techniques for proteins.

Small peptides are an exemplary system for exploring the relationship between structure and function in biology. A peptide is a sequence of amino acids. When the twenty naturally occurring amino acids are condensed into polymeric molecules they form a wide variety of three-dimensional configurations, each resulting from a particular amino acid sequence and solvent condition. The number of possible pentapeptides of the 20 naturally occurring amino acids, for example, is $20^5$ or 3.2 million different peptides. The likelihood that molecules of this size might be useful in receptor-binding studies is supported by epitope analysis studies showing that some antibodies recognize sequences as short as a few amino acids with high specificity. Furthermore, the average molecular weight of amino acids puts small peptides in the size range of many currently useful pharmaceutical products.

Pharmaceutical drug discovery is one type of research which relies on such a study of structure-activity relationships. In most cases, contemporary pharmaceutical research can be described as the process of discovering novel ligands with desirable patterns of specificity for biologically important receptors. Another example is research to discover new compounds for use in agriculture, such as pesticides and herbicides.

Sometimes, the solution to a rational process of designing ligands is difficult or unyielding. Prior methods of preparing large numbers of different polymers have been painstakingly slow when used at a scale sufficient to permit effective rational or random screening. For example, the "Merrifield" method (J. Am. Chem. Soc. (1963) 85:2149–2154, which is incorporated herein by reference for all purposes) has been used to synthesize peptides on a solid support. In the Merrifield method, an amino acid is covalently bonded to a support made of an insoluble polymer. Another amino acid with an alpha protected group is reacted with the covalently bonded amino acid to form a dipeptide. After washing, the protective group is removed and a third amino acid with an alpha protective group is added to the dipeptide. This process is continued until a peptide of a desired length and sequence is obtained. Using the Merrifield method, it is not economically practical to synthesize more than a handful of peptide sequences in a day.

To synthesize larger numbers of polymer sequences, it has also been proposed to use a series of reaction vessels for polymer synthesis. For example, a tubular reactor system may be used to synthesize a linear polymer on a solid phase support by automated sequential addition of reagents. This method still does not enable the synthesis of a sufficiently large number of polymer sequences for effective economical screening.

Methods of preparing a plurality of polymer sequences are also known in which a porous container encloses a known quantity of reactive particles, the particles being larger in size than porous of the container. The containers may be selectively reacted with desired materials to synthesize desired sequences of product molecules. As with other methods known in the art, this method cannot practically be used to synthesize a sufficient variety of polypeptides for effective screening.

Other techniques have also been described. These methods include the synthesis of peptides on 96 plastic pins which fit the format of standard microtiter plates. Unfortunately, while these techniques have been somewhat useful, substantial problems remain. For example, these methods continue to be limited in the diversity of sequences which can be economically synthesized and screened.

From the above, it is seen that an improved method and apparatus for synthesizing a variety of chemical sequences at known locations is desired.

SUMMARY OF THE INVENTION

An improved method and apparatus for the preparation of a variety of polymers is disclosed.

In one preferred embodiment, linker molecules are provided on a substrate. A terminal end of the linker molecules is provided with a reactive functional group protected with a photoremovable protective group. Using lithographic methods, the photoremovable protective group is exposed to light and removed from the linker molecules in first selected regions. The substrate is then washed or otherwise contacted with a first monomer that reacts with exposed functional groups on the linker molecules. In a preferred embodiment, the monomer is an amino acid containing a photoremovable protective group at its amino or carboxy terminus and the linker molecule terminates in an amino or carboxy acid group bearing a photoremovable protective group.

A second set of selected regions is, thereafter, exposed to light and the photoremovable protective group on the linker molecule/protected amino acid is removed at the second set of regions. The substrate is then contacted with a second monomer containing a photoremovable protective group for reaction with exposed functional groups. This process is repeated to selectively apply monomers until polymers of a desired length and desired chemical sequence are obtained. Photolabile groups are then optionally removed and the sequence is, thereafter, optionally capped. Side chain protective groups, if present, are also removed.

By using the lithographic techniques disclosed herein, it is possible to direct light to relatively small and precisely known locations on the substrate. It is, therefore, possible to synthesize polymers of a known chemical sequence at known locations on the substrate.

The resulting substrate will have a variety of uses including, for example, screening large numbers of polymers for biological activity. To screen for biological activity, the substrate is exposed to one or more receptors such as antibodies whole cells, receptors on vesicles, lipids, or any one of a variety of other receptors. The receptors are preferably labeled with, for example, a fluorescent marker, radioactive marker, or a labeled antibody reactive with the receptor. The location of the marker on the substrate is detected with, for example, photon detection or autoradiographic techniques. Through knowledge of the sequence of the material at the location where binding is detected, it is possible to quickly determine which sequence binds with the receptor and, therefore, the technique can be used to screen large numbers of peptides. Other possible applications of the inventions herein include diagnostics in which various antibodies for particular receptors would be placed on a substrate and, for example, blood sera would be screened for immune deficiencies. Still further applications include, for example, selective "doping" of organic materials in semiconductor devices, and the like.

In connection with one aspect of the invention an improved reactor system for synthesizing polymers is also disclosed. The reactor system includes a substrate mount which engages a substrate around a periphery thereof. The substrate mount provides for a reactor space between the substrate and the mount through or into which reaction fluids are pumped or flowed. A mask is placed on or focused on the substrate and illuminated so as to deprotect selected regions of the substrate in the reactor space. A monomer is pumped through the reactor space or otherwise contacted with the substrate and reacts with the deprotected regions. By selectively deprotecting regions on the substrate and flowing predetermined monomers through the reactor space, desired polymers at known locations may be synthesized.

Improved detection apparatus and methods are also disclosed. The detection method and apparatus utilize a substrate having a large variety of polymer sequences at known locations on a surface thereof. The substrate is exposed to a fluorescently labeled receptor which binds to one or more of the polymer sequences. The substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light. The means for detecting light fluoresced on the substrate may in some embodiments include a photon counter. The means for determining a location of the fluoresced light may include an x/y translation table for the substrate. Translation of the slide and data collection are recorded and managed by an appropriately programmed digital computer.

A further understanding of the nature and advantages of the inventions herein may be realized by reference to the remaining portions of the specification and the attached drawings.

BRIEF DESCRIPTION OF THE FIGURES

FIG. 1 illustrates masking and irradiation of a substrate at a first location. The substrate is shown in cross-section;

FIG. 2 illustrates the substrate after application of a monomer "A";

FIG. 3 illustrates irradiation of the substrate at a second location;

FIG. 4 illustrates the substrate after application of monomer "B";

FIG. 5 illustrates irradiation of the "A" monomer;

FIG. 6 illustrates the substrate after a second application of "B";

FIG. 7 illustrates a completed substrate;

FIGS. 8A and 8B illustrate alternative embodiments of a reactor system for forming a plurality of polymers on a substrate;

FIG. 9 illustrates a detection apparatus for locating fluorescent markers on the substrate;

FIGS. 10A–10M illustrate the method as it is applied to the production of the trimers of monomers "A" and "B";

FIGS. 11A, and 11B are fluorescence traces for standard fluorescent beads;

FIGS. 12A and 12B are fluorescence curves for NVOC (6-Nitroveratryloxycarbonyl) slides not exposed and exposed to light respectively;

FIGS. 13A to 13D are fluorescence plots of slides exposed through 100 $\mu$m, 50 $\mu$m, 20 $\mu$m, and 10 $\mu$m masks;

FIGS. 14A and 14B illustrate formation of YGGFL (a peptide of sequence $H_2$N-tyrosine-glycine-glycine-phenylalanine-leucine-$CO_2$H) and GGFL (a peptide of sequence $H_2$N-glycine-glycine-phenylalanine-leucine-$CO_2$H) followed by exposure to labeled Herz antibody (an antibody that recognizes YGGFL but not GGFL);

FIGS. 15A to 15D illustrate formation fluorescence plots of a slide with a checkerboard pattern of YGGFL and GGFL exposed to labeled Herz antibody. FIG. 15A illustrates a 500×500 $\mu$m mask which has been focused on the substrate according to FIG. 8A while FIG. 15B illustrates a 50×50 $\mu$m mask placed in direct contact with the substrate in accord with FIG. 8B;

FIG. 16 is a fluorescence plot of YGGFL and PGGFL synthesized in a 50 $\mu$m checkerboard pattern;

FIG. 17 is a fluorescence plot of YPGGFL and YGGFL synthesized in a 50 $\mu$m checkerboard pattern;

FIGS. 18A and 18B illustrate the mapping of sixteen sequences synthesized on two different glass slides;

FIG. 19 is a fluorescence plot of the slide illustrated in FIG. 18A; and

FIG. 20 is a fluorescence plot of the slide illustrated in FIG. 10B.

---

DETAILED DESCRIPTION OF THE PREFERRED EMBODIMENTS
CONTENTS

| | |
|---|---|
| I. | Glossary |
| II. | General |
| III. | Polymer Synthesis |
| IV. | Details of One Embodiment of a Reactor System |
| V. | Details of One Embodiment of a Fluorescent Detection Device |
| VI. | Determination of Relative Binding Strength of Receptors |
| VII. | Examples |
| | A. Slide Preparation |
| | B. Synthesis of Eight Trimers of "A" and "B" |
| | C. Synthesis of a Dimer of an Aminopropyl Group and a Fluorescent Group |
| | D. Demonstration of Signal Capability |
| | E. Determination of the Number of Molecules Per Unit Area |
| | F. Removal of NVOC and Attachment of a Fluorescent Marker |
| | G. Use of a Mask in Removal of NVOC |
| | H. Attachment of YGGFL and Subsequent Exposure to Herz Antibody and Goat Antimouse |
| | I. Monomer-by-Monomer Formation of YGGFL and Subsequent Exposure to Labeled Antibody |
| | J. Monomer-by-Monomer Synthesis of YGGFL and PGGFL |
| | K. Monomer-by Monomer Synthesis of YGGFL and YPGGFL |
| | L. Synthesis of an Array of Sixteen Different Amino Acid Sequences and Estimation of Relative Binding Affinity to Herz Antibody |
| VIII. | Illustrative Alternative Embodiment |
| IX. | Conclusion |

---

I. GLOSSARY

The following terms are intended to have the following general meanings as they are used herein:

1. Complementary: Refers to the topological compatibility or matching together of interacting surfaces of a ligand molecule and its receptor. Thus, the receptor and its ligand can be described as complementary, and furthermore, the contact surface characteristics are complementary to each other.
2. Epitope: The portion of an antigen molecule which is delineated by the area of interaction with the subclass of receptors known as antibodies.
3. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., steroids, etc.), hormone receptors, peptides, enzymes, enzyme substrates, cofactors, drugs (e.g., opiates etc.), lectins, sugars, oligonucleotides, nucleic acids, oligosaccharides, proteins, and monoclonal antibodies.
4. Monomer: A member of the set of small molecules which can be joined together to form a polymer. The set of monomers includes but is not restricted to, for example, the set of common L-amino acids, the set of D-amino acids, the set of synthetic amino acids, the set of nucleotides and the set of pentoses and hexoses. As used herein, monomers refers to any member of a basis set for synthesis of a polymer. For example, dimers of L-amino acids form a basis set of 400 monomers for synthesis of polypeptides. Different basis sets of monomers may be used at successive steps in the synthesis of a polymer.
5. Peptide: A polymer in which the monomers are alpha amino acids and which are joined together through amide bonds and alternatively referred to as a polypeptide. In the context of this specification it should be appreciated that the amino acids may be the L-optical isomer or the D-optical isomer. Peptides are more than two amino acid monomers long, and often more than 20 amino acid monomers long. Standard abbreviations for amino acids are used (e.g., P for proline). These abbreviations are included in Stryer, *Biochemstry*, Third Ed., 1988, which is incorporated herein by reference for all purposes.
6. Radiation: Energy which may be selectively applied including energy having a wavelength of between $10^{-14}$ and $10^4$ meters including, for example, electron beam radiation, gamma radiation, x-ray radiation, ultraviolet radiation, visible light, infrared radiation, microwave radiation, and radio waves. "Irradiation" refers to the application of radiation to a surface.
7. Receptor: A molecule that has an affinity for a given ligand. Receptors may be naturally-occuring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex.

Other examples of receptors which can be investigated by this invention include but are not restricted to:

a) Microorganism receptors: Determination of ligands which bind to receptors, such as specific transport proteins or enzymes essential to survival of microorganisms, is useful in a new class of antibiotics. Of particular value would be antibiotics against opportunistic fungi, protozoa, and those bacteria resistant to the antibiotics in current use.

b) Enzymes: For instance, the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the development of vaccines of which the immunogen is based on one or more of such sequences or lead to the development of related diagnostic agents or compounds useful in therapeutic treatments such as for auto-immune diseases (e.g., by blocking the binding of the "self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides are described in, for example, copending U.S. application Ser. No. 404,920, which is incorporated herein by reference for all purposes.

f) Hormone receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone which can only be obtained from cadavers or by recombinant DNA technology. other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

8. Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.

9. Protective Group: A material which is bound to a monomer unit and which may be spatially removed upon selective exposure to an activator such as electromagnetic radiation. Examples of protective groups with utility herein include Nitroveratryloxy carbonyl, Nitrobenzyloxy carbonyl, Dimethyl dimethoxybenzyloxy carbonyl, 5-Bromo-7-nitroindolinyl, o-Hydroxy-α-methyl cinnamoyl, and 2-Oxymethylene anthraquinone. Other examples of activators include ion beams, electric fields, magnetic fields, electron beams, x-ray, and the like.

10. Predefined Region: A predefined region is a localized area on a surface which is, was, or is intended to be activated for formation of a polymer. The predefined region may have any convenient shape, e.g., circular, rectangular, elliptical, wedge-shaped, etc. For the sake of brevity herein, "predefined regions" are sometimes referred to simply as "regions."

11. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor.

II. GENERAL

The present invention provides methods and apparatus for the preparation and use of a substrate having a plurality of polymer sequences in predefined regions. The invention is described herein primarily with regard to the preparation of molecules containing sequences of amino acids, but could readily be applied in the preparation of other polymers. Such polymers include, for example, both linear and cyclic polymers of nucleic acids, polysaccharides, phospholipids, and peptides having either α-, β-, or ω-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. In a preferred embodiment, the invention herein is used in the synthesis of peptides.

The prepared substrate may, for example, be used in screening a variety of polymers as ligands for binding with a receptor, although it will be apparent that the invention could be used for the synthesis of a receptor for binding with a ligand. The substrate disclosed herein will have a wide variety of other uses. Merely by way of example, the invention herein can be used in determining peptide and nucleic acid sequences which bind to proteins, finding sequence-specific binding drugs, identifying epitopes recognized by antibodies, and evaluation of a variety of drugs for clinical and diagnostic applications, as well as combinations of the above.

The invention preferably provides for the use of a substrate "S" with a surface. Linker molecules "L" are optionally provided on a surface of the substrate. The purpose of the linker molecules, in some embodiments, is to facilitate receptor recognition of the synthesized polymers.

Optionally, the linker molecules may be chemically protected for storage purposes. A chemical storage protective group such as t-BOC (t-butoxycarbonyl) may be used in some embodiments. Such chemical protective groups would be chemically removed upon exposure to, for example, acidic solution and would serve to protect the surface during storage and be removed prior to polymer preparation.

On the substrate or a distal end of the linker molecules, a functional group with a protective group $P_0$ is provided. The protective group $P_0$ may be removed upon exposure to radiation, electric fields, electric currents, or other activators to expose the functional group.

In a preferred embodiment, the radiation is ultraviolet (UV), infrared (IR), or visible light. As more fully described below, the protective group may alternatively be an electrochemically-sensitive group which may be removed in the presence of an electric field. In still further alternative embodiments, ion beams, electron beams, or the like may be used for deprotection.

In some embodiments, the exposed regions and, therefore, the area upon which each distinct polymer sequence is synthesized are smaller than about 1 cm² or less than 1 mm². In preferred embodiments the exposed area is less than about 10,000 $\mu$m² or, more preferably, less than 100 $\mu$m² and may, in some embodiments, encompass the binding site for as few as a single molecule. Within these regions, each polymer is preferably synthesized in a substantially pure form.

Concurrently or after exposure of a known region of the substrate to light, the surface is contacted with a first monomer unit $M_1$ which reacts with the functional group which has been exposed by the deprotection step. The first monomer includes a protective group $P_1$. $P_1$ may or may not be the same as $P_0$.

Accordingly, after a first cycle, known first regions of the surface may comprise the sequence:

$S-L-M_1-P_1$ while remaining regions of the surface comprise the sequence:

$S-L-P_0$.

Thereafter, second regions of the surface (which may include the first region) are exposed to light and contacted with a second monomer $M_2$ (which may or may not be the same as $M_1$) having a protective group $P_2$. $P_2$ may or may not be the same as $P_0$ and $P_1$. After this second cycle, different regions of the substrate may comprise one or more of the following sequences:

$S-L-M_1-M_2-P_2$ $S-L-M_2-P_2$ $S-L-M_1-P_1$ and/or $S-L-P_0$.

The above process is repeated until the substrate includes desired polymers of desired lengths. By controlling the locations of the substrate exposed to light and the reagents exposed to the substrate following exposure, the location of each sequence will be known.

Thereafter, the protective groups are removed from some or all of the substrate and the sequences are, optionally, capped with a capping unit C. The process results in a substrate having a surface with a plurality of polymers of the following general formula:

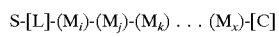

where square brackets indicate optional groups, and $M_i \ldots M_x$ indicates any sequence of monomers. The number of monomers could cover a wide variety of values, but in a preferred embodiment they will range from 2 to 100.

In some embodiments a plurality of locations on the substrate polymers are to contain a common monomer subsequence. For example, it may be desired to synthesize a sequence $S-M_1-M_2-M_3$ at first locations and a sequence $S-M_4-M_2-M_3$ at second locations. The process would commence with irradiation of the first locations followed by contacting with $M_1$-P, resulting in the sequence $S-M_1$-P at the first location. The second locations would then be irradiated and contacted with $M_4$-P, resulting in the sequence $S-M_4$-P at the second locations. Thereafter both the first and second locations would be irradiated and contacted with the dimer $M_2$-$M_3$, resulting in the sequence $S-M_1-M_2-M_3$ at the first locations and $S-M_4-M_2-M_3$ at the second locations. Of course, common subsequences of any length could be utilized including those in a range of 2 or more monomers, 2 to 100 monomers, 2 to 20 monomers, and a most preferred range of 2 to 3 monomers.

According to other embodiments, a set of masks is used for the first monomer layer and, thereafter, varied light wavelengths are used for selective deprotection. For example, in the process discussed above, first regions are first exposed through a mask and reacted with a first monomer having a first protective group $P_1$, which is removable upon exposure to a first wavelength of light (e.g., IR). Second regions are masked and reacted with a second monomer having a second protective group $P_2$, which is removable upon exposure to a second wavelength of light (e.g., UV). Thereafter, masks become unnecessary in the synthesis because the entire substrate may be exposed alternatively to the first and second wavelengths of light in the deprotection cycle.

The polymers prepared on a substrate according to the above methods will have a variety of uses including, for example, screening for biological activity. In such screening activities, the substrate containing the sequences is exposed to an unlabeled or labeled receptor such as an antibody, receptor on a cell, phospholipid vesicle, or any one of a variety of other receptors. In one preferred embodiment the polymers are exposed to a first, unlabeled receptor of interest and, thereafter, exposed to a labeled receptor-specific recognition element, which is, for example, an antibody. This process will provide signal amplification in the detection stage.

The receptor molecules may bind with one or more polymers on the substrate. The presence of the labeled receptor and, therefore, the presence of a sequence which binds with the receptor is detected in a preferred embodiment through the use of autoradiography, detection of fluorescence with a charge-coupled device, fluorescence microscopy, or the like. The sequence of the polymer at the locations where the receptor binding is detected may be used to determine all or part of a sequence which is complementary to the receptor.

Use of the invention herein is illustrated primarily with reference to screening for biological activity. The invention will, however, find many other uses. For example, the invention may be used in information storage (e.g., on optical disks), production of molecular electronic devices, production of stationary phases in separation sciences, production of dyes and brightening agents, photography, and in immobilization of cells, proteins, lectins, nucleic acids, polysaccharides and the like in patterns on a surface via molecular recognition of specific polymer sequences. By synthesizing the same compound in adjacent, progressively differing concentrations, a gradient will be established to control chemotaxis or to develop diagnostic dipsticks which, for example, titrate an antibody against an increasing amount of antigen. By synthesizing several catalyst molecules in close proximity, more efficient multistep conversions may be achieved by "coordinate immobilization." Coordinate immobilization also may be used for electron transfer systems, as well as to provide both structural integrity and other desirable properties to materials such as lubrication, wetting, etc.

According to alternative embodiments, molecular biodistribution or pharmacokinetic properties may be examined. For example, to assess resistance to intestinal or serum proteases, polymers may be capped with a fluorescent tag and exposed to biological fluids of interest.

III. POLYMER SYNTHESIS

FIG. 1 illustrates one embodiment of the invention disclosed herein in which a substrate 2 is shown in cross-section. Essentially, any conceivable substrate may be employed in the invention. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface is also chosen to provide appropriate light-absorbing characteristics. For instance, the substrate may be a polymerized Langmuir Blodgett film, functionalized glass, Si, Ge, GaAs, GaP, $SiO_2$ $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure. In a preferred embodiment the substrate is flat glass or single-crystal silicon with surface relief features of less than 10 Å.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light, be provided with reflective "mirror" structures for maximization of light collection from fluorescent sources, or the like.

Surfaces on the solid substrate will usually, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. Preferably, the surface will contain reactive groups, which could be carboxyl, amino, hydroxyl, or the like. Most preferably, the surface will be optically transparent and will have surface Si—OH functionalities, such as are found on silica surfaces.

The surface 4 of the substrate is preferably provided with a layer of linker molecules 6, although it will be understood that the linker molecules are not required elements of the invention. The linker molecules are preferably of sufficient length to permit polymers in a completed substrate to interact freely with molecules exposed to the substrate. The linker molecules should be 6–50 atoms long to provide sufficient exposure. The linker molecules may be, for example, aryl acetylene, ethylene glycol oligomers containing 2–10 monomer units, diamines, diacids, amino acids, or combinations thereof. Other linker molecules may be used in light of this disclosure.

According to alternative embodiments, the linker molecules are selected based upon their hydrophilic/hydrophobic properties to improve presentation of synthesized polymers to certain receptors. For example, in the case of a hydrophilic receptor, hydrophilic linker molecules will be preferred so as to permit the receptor to more closely approach the synthesized polymer.

According to another alternative embodiment, linker molecules are also provided with a photocleavable group at an intermediate position. The photocleavable group is preferably cleavable at a wavelength different from the protective group. This enables removal of the various polymers following completion of the synthesis by way of exposure to the different wavelengths of light.

The linker molecules can be attached to the substrate via carbon-carbon bonds using, for example, (poly)trifluorochloroethylene surfaces, or preferably, by siloxane bonds (using, for example, glass or silicon oxide surfaces). Siloxane bonds with the surface of the substrate may be formed in one embodiment via reactions of linker molecules bearing trichlorosilyl groups. The linker molecules may optionally be attached in an ordered array, i.e., as parts of the head groups in a polymerized Langmuir Blodgett film. In alternative embodiments, the linker molecules are adsorbed to the surface of the substrate.

The linker molecules and monomers used herein are provided with a functional group to which is bound a protective group. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating.

The protective group on the linker molecules may be selected from a wide variety of positive light-reactive groups preferably including nitro aromatic compounds such as o-nitrobenzyl derivatives or benzylsulfonyl. In a preferred embodiment, 6-nitroveratryloxycarbonyl (NVOC), 2-nitrobenzyloxycarbonyl (NBOC) or α,α-dimethyl-dimethoxybenzyloxycarbonyl (DDZ) is used. In one embodiment, a nitro aromatic compound containing a benzylic hydrogen ortho to the nitro group is used, i.e., a chemical of the form:

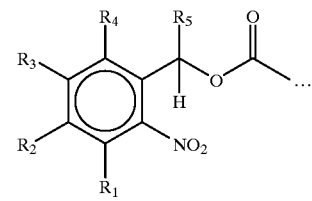

where $R_1$ is alkoxy, alkyl, halo, aryl, alkenyl, or hydrogen; $R_2$ is alkoxy, alkyl, halo, aryl, nitro, or hydrogen; $R_3$ is alkoxy, alkyl, halo, nitro, aryl, or hydrogen; $R_4$ is alkoxy, alkyl, hydrogen, aryl, halo, or nitro; and $R_5$ is alkyl, alkynyl, cyano, alkoxy, hydrogen, halo, aryl, or alkenyl. Other materials which may be used include o-hydroxy-α-methyl cinnamoyl derivatives. Photoremovable protective groups are described in, for example, Patchornik, *J. Am. Chem. Soc.* (1970) 92:6333 and Amit et al., *J. Org. Chem.* (1974) 39:192, both of which are incorporated herein by reference.

In an alternative embodiment the positive reactive group is activated for reaction with reagents in solution. For example, a 5-bromo-7-nitro indoline group, when bound to a carbonyl, undergoes reaction upon exposure to light at 420 nm.

In a second alternative embodiment, the reactive group on the linker molecule is selected from a wide variety of negative light-reactive groups including a cinammate group.

Alternatively, the reactive group is activated or deactivated by electron beam lithography, x-ray lithography, or any other radiation. Suitable reactive groups for electron beam lithography include sulfonyl. Other methods may be used including, for example, exposure to a current source. Other reactive groups and methods of activation may be used in light of this disclosure.

As shown in FIG. 1, the linking molecules are preferably exposed to, for example, light through a suitable mask 8 using photolithographic techniques of the type known in the semiconductor industry and described in, for example, Sze, *VLSI Technology*, McGraw-Hill (1983), and Mead et al., *Introduction to VLSI Systems*, Addison-Wesley (1980), which are incorporated herein by reference for all purposes. The light may be directed at either the surface containing the protective groups or at the back of the substrate, so long as the substrate is transparent to the wavelength of light needed for removal of the protective groups. In the embodiment shown in FIG. 1, light is directed at the surface of the substrate containing the protective groups. FIG. 1 illustrates the use of such masking techniques as they are applied to a positive reactive group so as to activate linking molecules and expose functional groups in areas 10a and 10b.

The mask 8 is in one embodiment a transparent support material selectively coated with a layer of opaque material. Portions of the opaque material are removed, leaving opaque material in the precise pattern desired on the substrate surface. The mask is brought into close proximity with, imaged on, or brought directly into contact with the substrate surface as shown in FIG. 1. "Openings" in the mask correspond to locations on the substrate where it is desired to remove photoremovable protective groups from the substrate. Alignment may be performed using conventional alignment techniques in which alignment marks (not shown) are used to accurately overlay successive masks with previous patterning steps, or more sophisticated techniques may be used. For example, interferometric techniques such as the one described in Flanders et al., "A New Interferometric Alignment Technique," *App. Phys. Lett.* (1977) 31:426–428, which is incorporated herein by reference, may be used.

To enhance contrast of light applied to the substrate, it is desirable to provide contrast enhancement materials between the mask and the substrate according to some embodiments. This contrast enhancement layer may comprise a molecule which is decomposed by light such as quinone diazide or a material which is transiently bleached at the wavelength of interest. Transient bleaching of materials will allow greater penetration where light is applied, thereby enhancing contrast. Alternatively, contrast enhancement may be provided by way of a cladded fiber optic bundle.

The light may be from a conventional incandescent source, a laser, a laser diode, or the like. If non-collimated sources of light are used it may be desirable to provide a thick- or multi-layered mask to prevent spreading of the light onto the substrate. It may, further, be desirable in some embodiments to utilize groups which are sensitive to different wavelengths to control synthesis. For example, by using groups which are sensitive to different wavelengths, it is possible to select branch positions in the synthesis of a polymer or eliminate certain masking steps. Several reactive groups along with their corresponding wavelengths for deprotection are provided in Table 1.

TABLE 1

| Group | Approximate Deprotection Wavelength |
| --- | --- |
| Nitroveratryloxy carbonyl (NVOC) | UV (300–400 nm) |
| Nitrobenzyloxy carbonyl (NBOC) | UV (300–350 nm) |
| Dimethyl dimethoxybenzyloxy carbonyl | UV (280–300 nm) |
| 5-Bromo-7-nitroindolinyl | UV (420 nm) |
| o-Hydroxy-α-methyl cinnamoyl | UV (300–350 nm) |
| 2-Oxymethylene anthraquinone | UV (350 nm) |

While the invention is illustrated primarily herein by way of the use of a mask to illuminate selected regions the substrate, other techniques may also be used. For example, the substrate may be translated under a modulated laser or diode light source. Such techniques are discussed in, for example, U.S. Pat. No. 4,719,615 (Feyrer et al.), which is incorporated herein by reference. In alternative embodiments a laser galvanometric scanner is utilized. In other embodiments, the synthesis may take place on or in contact with a conventional liquid crystal (referred to herein as a "light valve") or fiber optic light sources. By appropriately modulating liquid crystals, light may be selectively controlled so as to permit light to contact selected regions of the substrate. Alternatively, synthesis may take place on the end of a series of optical fibers to which light is selectively applied. Other means of controlling the location of light exposure will be apparent to those of skill in the art.

The substrate may be irradiated either in contact or not in contact with a solution (not shown) and is, preferably, irradiated in contact with a solution. The solution contains reagents to prevent the by-products formed by irradiation from interfering with synthesis of the polymer according to some embodiments. Such by-products might include, for example, carbon dioxide, nitrosocarbonyl compounds, styrene derivatives, indole derivatives, and products of their photochemical reactions. Alternatively, the solution may contain reagents used to match the index of refraction of the substrate. Reagents added to the solution may further include, for example, acidic or basic buffers, thiols, substituted hydrazines and hydroxylamines, reducing agents (e.g., NADH) or reagents known to react with a given functional group (e.g., aryl nitroso+glyoxylic acid→aryl formhydroxamate+$CO_2$).

Either concurrently with or after the irradiation step, the linker molecules are washed or otherwise contacted with a first monomer, illustrated by "A" in regions 12a and 12b in FIG. 2. The first monomer reacts with the activated functional groups of the linkage molecules which have been exposed to light. The first monomer, which is preferably an amino acid, is also provided with a photoprotective group. The photoprotective group on the monomer may be the same as or different than the protective group used in the linkage molecules, and may be selected from any of the above-described protective groups. In one embodiment, the protective groups for the A monomer is selected from the group NBOC and NVOC.

As shown in FIG. 3, the process of irradiating is thereafter repeated, with a mask repositioned so as to remove linkage protective groups and expose functional groups in regions 14a and 14b which are illustrated as being regions which were protected in the previous masking step. As an alternative to repositioning of the first mask, in many embodiments a second mask will be utilized. In other alternative embodiments, some steps may provide for illuminating a common region in successive steps. As shown in FIG. 3, it may be desirable to provide separation between irradiated regions. For example, separation of about 1–5 μm may be appropriate to account for alignment tolerances.

As shown in FIG. 4, the substrate is then exposed to a second protected monomer "B," producing B regions 16a and 16b. Thereafter, the substrate is again masked so as to remove the protective groups and expose reactive groups on A region 12a and B region 16b. The substrate is again exposed to monomer B, resulting in the formation of the structure shown in FIG. 6. The dimers B-A and B-B have been produced on the substrate.

A subsequent series of masking and contacting steps similar to those described above with A (not shown) provides the structure shown in FIG. 7. The process provides all possible dimers of B and A, i.e., B-A, A-B, A-A, and B-B.

The substrate, the area of synthesis, and the area for synthesis of each individual polymer could be of any size or shape. For example, squares, ellipsoids, rectangles, triangles, circles, or portions thereof, along with irregular geometric shapes, may be utilized. Duplicate synthesis areas may also be applied to a single substrate for purposes of redundancy.

In one embodiment the regions 12a, 12b, and 16a, 16b on the substrate will have a surface area of between about 1 cm$^2$ and 10$^{-10}$ cm$^2$. In some embodiments the regions 12 and 16 have areas of less than about 10$^{-1}$ cm$^2$, 10$^{-2}$ cm$^2$, 10$^{-3}$ cm$^2$, 10$^{-4}$ cm$^2$, 10$^{-5}$ cm$^2$, 10$^{-6}$ cm$^2$, 10$^{-7}$ cm$^2$, 10$^{-8}$ cm$^2$, or 10$^{-10}$ cm$^2$. In a preferred embodiment, the regions 12 and 16 are between about 10×10 μm and 500×500 μm.

In some embodiments a single substrate supports more than about 10 different monomer sequences and preferably more than about 100 different monomer sequences, although in some embodiments more than about 10$^3$, 10$^4$, 10$^5$, 10$^6$, 10$^7$, or 10$^8$ different sequences are provided on a substrate. Of course, within a region of the substrate in which a monomer sequence is synthesized, it is preferred that the monomer sequence be substantially pure. In some embodiments, regions of the substrate contain polymer sequences which are at least about 1%, 5%, 10%, 15%, 20%, 25%, 30%, 35%, 40%, 45%, 50%, 60%, 70%, 80%, 90%, 95%, 96%, 97%, 98%, or 99% pure.

According to some embodiments, several sequences are intentionally provided within a single region so as to provide an initial screening for biological activity, after which materials within regions exhibiting significant binding are further evaluated.

IV. DETAILED OF ONE EMBODIMENT OF A REACTOR SYSTEM

FIG. 8A schematically illustrates a preferred embodiment of a reactor system 100 for synthesizing polymers on the prepared substrate in accordance with one aspect of the invention. The reactor system includes a body 102 with a cavity 104 on a surface thereof. In preferred embodiments the cavity 104 is between about 50 and 1000 μm deep with a depth of about 500 μm preferred.

The bottom of the cavity is preferably provided with an array of ridges 106 which extend both into the plane of the Figure and parallel to the plane of the Figure. The ridges are preferably about 50 to 200 μm deep and spaced at about 2 to 3 mm. The purpose of the ridges is to generate turbulent flow for better mixing. The bottom surface of the cavity is preferably light absorbing so as to prevent reflection of impinging light.

A substrate 112 is mounted above the cavity 104. The substrate is provided along its bottom surface 114 with a photoremovable protective group such as NVOC with or without an intervening linker molecule. The substrate is preferably transparent to a wide spectrum of light, but in some embodiments is transparent only at a wavelength at which the protective group may be removed (such as UV in the case of NVOC). The substrate in some embodiments is a conventional microscope glass slide or cover slip. The substrate is preferably as thin as possible, while still providing adequate physical support. Preferably, the substrate is less than about 1 mm thick, more preferably less than 0.5 mm thick, more preferably less than 0.1 mm thick, and most preferably less than 0.05 mm thick. In alternative preferred embodiments, the substrate is quartz or silicon.

The substrate and the body serve to seal the cavity except for an inlet port 108 and an outlet port 110. The body and the substrate may be mated for sealing in some embodiments with one or more gaskets. According to a preferred embodiment, the body is provided with two concentric gaskets and the intervening space is held at vacuum to ensure mating of the substrate to the gaskets.

Fluid is pumped through the inlet port into the cavity by way of a pump 116 which may be, for example, a model no. B-120-S made by Eldex Laboratories. Selected fluids are circulated into the cavity by the pump, through the cavity, and out the outlet for recirculation or disposal. The reactor may be subjected to ultrasonic radiation and/or heated to aid in agitation in some embodiments.

Above the substrate 112, a lens 120 is provided which may be, for example, a 2" 100 mm focal length fused silica lens. For the sake of a compact system, a reflective mirror 122 may be provided for directing light from a light source 124 onto the substrate. Light source 124 may be, for example, a Xe(Hg) light source manufactured by Oriel and having model no. 66024. A second lens 126 may be provided for the purpose of projecting a mask image onto the substrate in combination with lens 120. This form of lithography is referred to herein as projection printing. As will be apparent from this disclosure, proximity printing and the like may also be used according to some embodiments.

Light from the light source is permitted to reach only selected locations on the substrate as a result of mask 128. Mask 128 may be, for example, a glass slide having etched chrome thereon. The mask 128 in one embodiment is provided with a grid of transparent locations and opaque locations. Such masks may be manufactured by, for example, Photo Sciences, Inc. Light passes freely through the transparent regions of the mask, but is reflected from or absorbed by other regions. Therefore, only selected regions of the substrate are exposed to light.

As discussed above, light valves (LCD's) may be used as an alternative to conventional masks to selectively expose regions of the substrate. Alternatively, fiber optic faceplates such as those available from Schott Glass, Inc, may be used for the purpose of contrast enhancement of the mask or as the sole means of restricting the region to which light is applied. Such faceplates would be placed directly above or on the substrate in the reactor shown in FIG. 8A. In still further embodiments, flys-eye lenses, tapered fiber optic faceplates, or the like, may be used for contrast enhancement.

In order to provide for illumination of regions smaller than a wavelength of light, more elaborate techniques may be utilized. For example, according to one preferred embodiment, light is directed at the substrate by way of molecular microcrystals on the tip of, for example, micropipettes. Such devices are disclosed in Lieberman et al., "A Light Source Smaller Than the Optical Wavelength," *Science* (1990) 247:59–61, which is incorporated herein by reference for all purposes.

In operation, the substrate is placed on the cavity and sealed thereto. All operations in the process of preparing the substrate are carried out in a room lit primarily or entirely by light of a wavelength outside of the light range at which the protective group is removed. For example, in the case of NVOC, the room should be lit with a conventional dark room light which provides little or no UV light. All operations are preferably conducted at about room temperature.

A first, deprotection fluid (without a monomer) is circulated through the cavity. The solution preferably is of 5 mM sulfuric acid in dioxane solution which serves to keep exposed amino groups protonated and decreases their reactivity with photolysis by-products. Absorptive materials such as N,N-diethylamino 2,4-dinitrobenzene, for example, may be included in the deprotection fluid which serves to absorb light and prevent reflection and unwanted photolysis.

The slide is, thereafter, positioned in a light raypath from the mask such that first locations on the substrate are illuminated and, therefore, deprotected. In preferred embodiments the substrate is illuminated for between about 1 and 15 minutes with a preferred illumination time of about 10 minutes at 10–20 mW/cm$^2$ with 365 nm light. The slides are neutralized (i.e., brought to a pH of about 7) after photolysis with, for example, a solution of di-isopropylethylamine (DIEA) in methylene chloride for about 5 minutes.

The first monomer is then placed at the first locations on the substrate. After irradiation, the slide is removed, treated in bulk, and then reinstalled in the flow cell. Alternatively, a fluid containing the first monomer, preferably also protected by a protective group, is circulated through the cavity by way of pump 116. If, for example, it is desired to attach the amino acid Y to the substrate at the first locations, the amino acid Y (bearing a protective group on its α-nitrogen), along with reagents used to render the monomer reactive, and/or a carrier, is circulated from a storage container 118, through the pump, through the cavity, and back to the inlet of the pump.

The monomer carrier solution is, in a preferred embodiment, formed by mixing of a first solution (referred to herein as solution "A") and a second solution (referred to herein as solution "B"). Table 2 provides an illustration of a mixture which may be used for solution A.

TABLE 2

Representative Monomer Carrier Solution "A"

100 mg NVOC amino protected amino acid
37 mg HOBT (1-Hydroxybenzotriazole)
250 μl DMF (Dimethylformamide)
86 μl DIEA (Diisopropylethylamine)

The composition of solution B is illustrated in Table 3. Solutions A and B are mixed and allowed to react at room temperature for about 8 minutes, then diluted with 2 ml of DMF, and 500 μl are applied to the surface of the slide or the solution is circulated through the reactor system and allowed to react for about 2 hours at room temperature. The slide is then washed with DMF, methylene chloride and ethanol.

TABLE 3

Representative Monomer Carrier Solution "B"

250 μl DMF
111 mg BOP (Benzotriazolyl-n-oxy-tris (dimethylamino) phosphoniumhexafluorophosphate)

As the solution containing the monomer to be attached is circulated through the cavity, the amino acid or other monomer will react at its carboxy terminus with amino groups on the regions of the substrate which have been deprotected. Of course, while the invention is illustrated by way of circulation of the monomer through the cavity, the invention could be practiced by way of removing the slide from the reactor and submersing it in an appropriate monomer solution.

After addition of the first monomer, the solution containing the first amino acid is then purged from the system. After circulation of a sufficient amount of the DMF/methylene chloride such that removal of the amino acid can be assured (e.g., about 50x times the volume of the cavity and carrier lines), the mask or substrate is repositioned, or a new mask is utilized such that second regions on the substrate will be exposed to light and the light 124 is engaged for a second exposure. This will deprotect second regions on the substrate and the process is repeated until the desired polymer sequences have been synthesized.

The entire derivatized substrate is then exposed to a receptor of interest, preferably labeled with, for example, a fluorescent marker, by circulation of a solution or suspension of the receptor through the cavity or by contacting the surface of the slide in bulk. The receptor will preferentially bind to certain regions of the substrate which contain complementary sequences.

Antibodies are typically suspended in what is commonly referred to as "supercocktail," which may be, for example, a solution of about 1% BSA (bovine serum albumin), 0.5% Tween™ Non-ionic detergent in PBS (phosphate buffered saline) buffer. The antibodies are diluted into the supercocktail buffer to a final concentration of, for example, about 0.1 to 4 μg/ml.

FIG. 8B illustrates an alternative preferred embodiment of the reactor shown in FIG. 8A. According to this embodiment, the mask 128 is placed directly in contact with the substrate. Preferably, the etched portion of the mask is placed face down so as to reduce the effects of light dispersion. According to this embodiment, the lenses 120 and 126 are not necessary because the mask is brought into close proximity with the substrate.

For purposes of increasing the signal-to-noise ratio of the technique, some embodiments of the invention provide for exposure of the substrate to a first labeled or unlabeled receptor followed by exposure of a labeled, second receptor (e.g., an antibody) which binds at multiple sites on the first receptor. If, for example, the first receptor is an antibody derived from a first species of an animal, the second receptor is an antibody derived from a second species directed to epitopes associated with the first species. In the case of a mouse antibody, for example, fluorescently labeled goat antibody or antiserum which is antimouse may be used to bind at multiple sites on the mouse antibody, providing several times the fluorescence compared to the attachment of a single mouse antibody at each binding site. This process may be repeated again with additional antibodies (e.g., goat-mouse-goat, etc.) for further signal amplification.

In preferred embodiments an ordered sequence of masks is utilized. In some embodiments it is possible to use as few as a single mask to synthesize all of the possible polymers of a given monomer set.

If, for example, it is desired to synthesize all 16 dinucleotides from four bases, a 1 cm square synthesis region is divided conceptually into 16 boxes, each 0.25 cm wide. Denote the four monomer units by A, B, C, and D. The first reactions are carried out in four vertical columns, each 0.25 cm wide. The first mask exposes the left-most column of boxes, where A is coupled. The second mask exposes the next column, where B is coupled; followed by a third mask, for the C column; and a final mask that exposes the right-most column, for D. The first, second, third, and fourth masks may be a single mask translated to different locations.

The process is repeated in the horizontal direction for the second unit of the dimer. This time, the masks allow exposure of horizontal rows, again 0.25 cm wide. A, B, C, and D are sequentially coupled using masks that expose horizontal fourths of the reaction area. The resulting substrate contains all 16 dinucleotides of four bases.

The eight masks used to synthesize the dinucleotide are related to one another by translation or rotation. In fact, one mask can be used in all eight steps if it is suitably rotated and translated. For example, in the example above, a mask with a single transparent region could be sequentially used to expose each of the vertical columns, translated 90°, and then sequentially used to allow exposure of the horizontal rows.

Tables 4 and 5 provide a simple computer program in Quick Basic for planning a masking program and a sample output, respectively, for the synthesis of a polymer chain of three monomers ("residues") having three different monomers in the first level, four different monomers in the second level, and five different monomers in the third level in a striped pattern. The output of the program is the number of cells, the number of "stripes" (light regions) on each mask, and the amount of translation required for each exposure of the mask.

TABLE 4

Mask Strategy Program

```
DEFINT A–Z
DIM b(20), w(20), 1(500)
F$ = "LPT1:"
OPEN f$ FOR OUTPUT AS #1
jmax = 3            'Number of residues
b(1) = 3: b(2) = 4: b(3) = 5         'Number of building blocks for res 1,2,3
g = 1: 1max(1) = 1
FOR j = 1 TO jmax: g= g * b(j): NEXT j
w(0) = 0: w(1) = g / b(1)
PRINT #1, "MASK2.BAS ", DATE$, TIME$: PRINT #1,
PRINT #1, USING "Number of residues=##"; jmax
FOR j = 1 TO jmax
PRINT #1, USING "        Residue ##        ## building blocks"; j; b(j)
NEXT j
PRINT #1, "
PRINT #1, USING "Number of cells=####"; g: PRINT #1,
FOR j = 2 TO jmax
1max(j) = 1max(j − 1) * b(j − 1)
w(j) = w(j − 1) / b(j)
NEXT j
FOR j = 1 TO jmax
PRINT #1, USING "Mask for residue ##"; j: PRINT #1,
PRINT #1, USING " Number of stripes=###"; 1max(j)
PRINT #1, USING " Width of each stripe=###"; w(j)
FOR 1 = 1 TO 1max(j)
a = 1 + (1 − 1) * w(j − 1)
ae = a + w(j) − 1
PRINT #1, USING "      Stripe ## begins at location ### and ends at ###"; 1; a; ae
NEXT 1
PRINT #1,
PRINT #1, USING " For each of ## building blocks, translate mask by ## cell(s)"; b(j); w(j),
PRINT #1, : PRINT #1, : PRINT #1,
NEXT j
```

©Copyright 1990, Affymax N.V.

TABLE 5

Masking Strategy Output

Number of residues= 3
    Residue 1    3 building blocks
    Residue 2    4 building blocks
    Residue 3    5 building blocks
Number of cells= 60
Mask for residue 1
    Number of stripes= 1
    Width of each stripe= 20
    Stripe    1 begins at location    1 and ends at    20
    For each of 3 building blocks, translate mask by 20 cell(s)

TABLE 5-continued

Masking Strategy Output

Mask for residue 2
    Number of stripes= 3
    Width of each stripe= 5
    Stripe    1 begins at location    1 and ends at    5
    Stripe    2 begins at location    21 and ends at    25
    Stripe    3 begins at location    41 and ends at    45
    For each of 4 building blocks, translate mask by 5 cell(s)
Mask for residue 3
    Number of stripes= 12
    Width of each stripe= 1
    Stripe    1 begins at location    1 and ends at    1
    Stripe    2 begins at location    6 and ends at    6
    Stripe    3 begins at location    11 and ends at    11
    Stripe    4 begins at location    16 and ends at    16
    Stripe    5 begins at location    21 and ends at    21
    Stripe    6 begins at location    26 and ends at    26
    Stripe    7 begins at location    31 and ends at    31
    Stripe    8 begins at location    36 and ends at    36
    Stripe    9 begins at location    41 and ends at    41
    Stripe    10 begins at location    46 and ends at    46
    Stripe    11 begins at location    51 and ends at    51
    Stripe    12 begins at location    56 and ends at    56
For each of 5 building blocks, translate mask by 1 cell(s)

© Copyright 1990, Affymax N.V.

V. DETAILS OF ONE EMBODIMENT OF A FLUORESCENT DETECTION DEVICE

FIG. 9 illustrates a fluorescent detection device for detecting fluorescently labeled receptors on a substrate. A substrate 112 is placed on an x/y translation table 202. In a preferred embodiment the x/y translation table is a model no. PM500-A1 manufactured by Newport Corporation. The x/y translation table is connected to and controlled by an appropriately programmed digital computer 204 which may be, for example, an appropriately programmed IBM PC/AT or AT compatible computer. Of course, other computer systems, special purpose hardware, or the like could readily be substituted for the AT computer used herein for illustration. Computer software for the translation and data collection functions described herein can be provided based on commercially available software including, for example, "Lab Windows" licensed by National Instruments, which is incorporated herein by reference for all purposes.

The substrate and x/y translation table are placed under a microscope 206 which includes one or more objectives 208. Light (about 488 nm) from a laser 210, which in some embodiments is a model no. 2020-05 argon ion laser manufactured by Spectraphysics, is directed at the substrate by a dichroic mirror 207 which passes greater than about 520 nm light but reflects 488 nm light. Dichroic mirror 207 may be, for example, a model no. FT510 manufactured by Carl Zeiss. Light reflected from the mirror then enters the microscope 206 which may be, for example, a model no. Axioscop 20 manufactured by Carl Zeiss. Fluorescein-marked materials on the substrate will fluoresce >488 nm light, and the fluoresced light will be collected by the microscope and passed through the mirror. The fluorescent light from the substrate is then directed through a wavelength filter 209 and, thereafter through an aperture plate 211. Wavelength filter 209 may be, for example, a model no. OG530 manufactured by Melles Griot and aperture plate 211 may be, for example, a model no. 477352/477380 manufactured by Carl Zeiss.

The fluoresced light then enters a photomultiplier tube 212 which in some embodiments is a model no. R943-02 manufactured by Hamamatsu, the signal is amplified in preamplifier 214 and photons are counted by photon counter 216. The number of photons is recorded as a function of the location in the computer 204. Pre-Amp 214 may be, for example, a model no. SR440 manufactured by Stanford Research Systems and photon counter 216 may be a model no. SR400 manufactured by Stanford Research Systems. The substrate is then moved to a subsequent location and the process is repeated. In preferred embodiments the data are acquired every 1 to 100 $\mu$m with a data collection diameter of about 0.8 to 10 $\mu$m preferred. In embodiments with sufficiently high fluorescence, a CCD (change coupled device) detector with broadfield illumination is utilized.

By counting the number of photons generated in a given area in response to the laser, it is possible to determine where fluorescent marked molecules are located on the substrate. Consequently, for a slide which has a matrix of polypeptides, for example, synthesized on the surface thereof, it is possible to determine which of the polypeptides is complementary to a fluorescently marked receptor.

According to preferred embodiments, the intensity and duration of the light applied to the substrate is controlled by varying the laser power and scan stage rate for improved signal-to-noise ratio by maximizing fluorescence emission and minimizing background noise.

While the detection apparatus has been illustrated primarily herein with regard to the detection of marked receptors, the invention will find application in other areas. For example, the detection apparatus disclosed herein could be used in the fields of catalysis, DNA or protein gel scanning, and the like.

VI. DETERMINATION OF RELATIVE BINDING STRENGTH OF RECEPTORS

The signal-to-noise ratio of the present invention is sufficiently high that not only can the presence or absence of a receptor on a ligand be detected, but also the relative binding affinity of receptors to a variety of sequences can be determined.

In practice it is found that a receptor will bind to several peptide sequences in an array, but will bind much more strongly to some sequences than others. Strong binding affinity will be evidenced herein by a strong fluorescent or radiographic signal since many receptor molecules will bind in a region of a strongly bound ligand. Conversely, a weak binding affinity will be evidenced by a weak fluorescent or radiographic signal due to the relatively small number of receptor molecules which bind in a particular region of a substrate having a ligand with a weak binding affinity for the receptor. Consequently, it becomes possible to determine relative binding avidity (or affinity in the case of univalent interactions) of a ligand herein by way of the intensity of a fluorescent or radiographic signal in a region containing that ligand.

Semiquantitative data on affinities might also be obtained by varying washing conditions and concentrations of the receptor. This would be done by comparison to known ligand receptor pairs, for example.

VII. EXAMPLES

The following examples are provided to illustrate the efficacy of the inventions herein. All operations were conducted at about ambient temperatures and pressures unless indicated to the contrary.

A. Slide Preparation

Before attachment of reactive groups it is preferred to clean the substrate which is, in a preferred embodiment a glass substrate such as a microscope slide or cover slip. According to one embodiment the slide is soaked in an alkaline bath consisting of, for example, 1 liter of 95% ethanol with 120 ml of water and 120 grams of sodium hydroxide for 12 hours. The slides are then washed under running water and allowed to air dry, and rinsed once with a solution of 95% ethanol.

The slides are then aminated with, for example, aminopropyltriethoxysilane for the purpose of attaching amino groups to the glass surface on linker molecules, although any omega functionalized silane could also be used for this purpose. In one embodiment 0.1% aminopropyltriethoxysilane is utilized, although solutions with concentrations from $10^{-7}\%$ to 10% may be used, with about $10^{-3}\%$ to 2% preferred. A 0.1% mixture is prepared by adding to 100 ml of a 95% ethanol/5% water mixture, 100 microliters ($\mu$l) of aminopropyltriethoxysilane. The mixture is agitated at about ambient temperature on a rotary shaker for about 5 minutes. 500 $\mu$l of this mixture is then applied to the surface of one side of each cleaned slide. After 4 minutes, the slides are decanted of this solution and rinsed three times by dipping in, for example, 100% ethanol.

After the plates dry, they are placed in a 110–120° C. vacuum oven for about 20 minutes, and then allowed to cure at room temperature for about 12 hours in an argon environment. The slides are then dipped into DMF (dimethylformamide) solution, followed by a thorough washing with methylene chloride.

The aminated surface of the slide is then exposed to about 500 µl of, for example, a 30 millimolar (mM) solution of NVOC-GABA (gamma amino butyric acid) NHS (N-hydroxysuccinimide) in DMF for attachment of a NVOC-GABA to each of the amino groups.

The surface is washed with, for example, DMF, methylene chloride, and ethanol.

Any unreacted aminopropyl silane on the surface—that is, those amino groups which have not had the NVOC-GABA attached—are now capped with acetyl groups (to prevent further reaction) by exposure to a 1:3 mixture of acetic anhydride in pyridine for 1 hour. Other materials which may perform this residual capping function include trifluoroacetic anhydride, formicacetic anhydride, or other reactive acylating agents. Finally, the slides are washed again with DMF, methylene chloride, and ethanol.

B. Synthesis of Eight Trimers of "A" and "B"

FIG. 10 illustrates a possible synthesis of the eight trimers of the two-monomer set: gly, phe (represented by "A" and "B," respectively). A glass slide bearing silane groups terminating in 6-nitroveratryloxycarboxamide (NVOC—NH) residues is prepared as a substrate. Active esters (pentafluorophenyl, OBt, etc.) of gly and phe protected at the amino group with NVOC are prepared as reagents. While not pertinent to this example, if side chain protecting groups are required for the monomer set, these must not be photoreactive at the wavelength of light used to protect the primary chain.

For a monomer set of size n, n×l cycles are required to synthesize all possible sequences of length l. A cycle consists of:

1. Irradiation through an appropriate mask to expose the amino groups at the sites where the next residue is to be added, with appropriate washes to remove the by-products of the deprotection.
2. Addition of a single activated and protected (with the same photochemically-removable group) monomer, which will react only at the sites addressed in step 1, with appropriate washes to remove the excess reagent from the surface.

The above cycle is repeated for each member of the monomer set until each location on the surface has been extended by one residue in one embodiment. In other embodiments, several residues are sequentially added at one location before moving on to the next location. Cycle times will generally be limited by the coupling reaction rate, now as short as 20 min in automated peptide synthesizers. This step is optionally followed by addition of a protecting group to stabilize the array for later testing. For some types of polymers (e.g., peptides), a final deprotection of the entire surface (removal of photoprotective side chain groups) may be required.

More particularly, as shown in FIG. 10A, the glass 20 is provided with regions 22, 24, 26, 28, 30, 32, 34, and 36. Regions 30, 32, 34, and 36 are masked, as shown in FIG. 10B and the glass is irradiated and exposed to a reagent containing "A" (e.g., gly), with the resulting structure shown in FIG. 10C. Thereafter, regions 22, 24, 26, and 28 are masked, the glass is irradiated (as shown in FIG. 10D) and exposed to a reagent containing "B" (e.g., phe), with the resulting structure shown in FIG. 10E. The process proceeds, consecutively masking and exposing the sections as shown until the structure shown in FIG. 10M is obtained. The glass is irradiated and the terminal groups are, optionally, capped by acetylation. As shown, all possible trimers of gly/phe are obtained.

In this example, no side chain protective group removal is necessary. If it is desired, side chain deprotection may be accomplished by treatment with ethanedithiol and trifluoroacetic acid.

In general, the number of steps needed to obtain a particular polymer chain is defined by:

$$n \times l \qquad (1)$$

where:

n=the number of monomers in the basis set of monomers, and l=the number of monomer units in a polymer chain.

Conversely, the synthesized number of sequences of length l will be:

$$n^l. \qquad (2)$$

Of course, greater diversity is obtained by using masking strategies which will also include the synthesis of polymers having a length of less than l. If, in the extreme case, all polymers having a length less than or equal to l are synthesized, the number of polymers synthesized will be:

$$n^l + n^{l-1} + \ldots + n^1. \qquad (3)$$

The maximum number of lithographic steps needed will generally be n for each "layer" of monomers, i.e., the total number of masks (and, therefore, the number of lithographic steps) needed will be n×l. The size of the transparent mask regions will vary in accordance with the area of the substrate available for synthesis and the number of sequences to be formed. In general, the size of the synthesis areas will be:

$$\text{size of synthesis areas}=(A)/(\text{Sequences})$$

where:

A is the total area available for synthesis; and

Sequences is the number of sequences desired in the area.

It will be appreciated by those of skill in the art that the above method could readily be used to simultaneously produce thousands or millions of oligomers on a substrate using the photolithographic techniques disclosed herein. Consequently, the method results in the ability to practically test large numbers of, for example, di, tri, tetra, penta, hexa, hepta, octapeptides, dodecapeptides, or larger polypeptides (or correspondingly, polynucleotides).

The above example has illustrated the method by way of a manual example. It will of course be appreciated that automated or semi-automated methods could be used. The substrate would be mounted in a flow cell for automated addition and removal of reagents, to minimize the volume of reagents needed, and to more carefully control reaction conditions. Successive masks could be applied manually or automatically.

C. Synthesis of a Dimer of an Aminopropyl Group and a Fluorescent Group

In synthesizing the dimer of an aminopropyl group and a fluorescent group, a functionalized durapore membrane was used as a substrate. The durapore membrane was a polyvinylidine difluoride with aminopropyl groups. The aminopropyl groups were protected with the DDZ group by reaction of the carbonyl chloride with the amino groups, a reaction readily known to those of skill in the art. The surface bearing these groups was placed in a solution of THF and contacted with a mask bearing a checkerboard pattern of 1 mm opaque and transparent regions. The mask was exposed to ultraviolet light having a wavelength down to at least about 280 nm for about 5 minutes at ambient temperature, although a wide range of exposure times and temperatures may be appropriate in various embodiments of the invention. For example, in one embodiment, an exposure time of between about 1 and 5000 seconds may be used at process temperatures of between −70 and +50° C.

In one preferred embodiment, exposure times of between about 1 and 500 seconds at about ambient pressure are used. In some preferred embodiments, pressure above ambient is used to prevent evaporation.

The surface of the membrane was then washed for about 1 hour with a fluorescent label which included an active ester bound to a chelate of a lanthanide. Wash times will vary over a wide range of values from about a few minutes to a few hours. These materials fluoresce in the red and the green visible region. After the reaction with the active ester in the fluorophore was complete, the locations in which the fluorophore was bound could be visualized by exposing them to ultraviolet light and observing the red and the green fluorescence. It was observed that the derivatized regions of the substrate closely corresponded to the original pattern of the mask.

D. Demonstration of Signal Capability

Signal detection capability was demonstrated using a low-level standard fluorescent bead kit manufactured by Flow Cytometry Standards and having model no. 824. This kit includes 5.8 $\mu$m diameter beads, each impregnated with a known number of fluorescein molecules.

One of the beads was placed in the illumination field on the scan stage as shown in FIG. 9 in a field of a laser spot which was initially shuttered. After being positioned in the illumination field, the photon detection equipment was turned on. The laser beam was unblocked and it interacted with the particle bead, which then fluoresced. Fluorescence curves of beads impregnated with 7,000; 13,000; fluorescein molecules, are shown in FIGS. 11A, 11B, respectively. On each curve, traces for beads without fluorescein molecules are also shown. These experiments were performed with 488 nm excitation, with 100 $\mu$W of laser power. The light was focused through a 40 power 0.75 NA objective.

The fluorescence intensity in all cases started off at a high value and then decreased exponentially. The fall-off in intensity is due to photobleaching of the fluorescein molecules. The traces of beads without fluorescein molecules are used for background subtraction. The difference in the initial exponential decay between labeled and nonlabeled beads is integrated to give the total number of photon counts, and this number is related to the number of molecules per bead. Therefore, it is possible to deduce the number of photons per fluorescein molecule that can be detected. For the curves illustrated in FIGS. 11A and 11B, this calculation indicates the radiation of about 40 to 50 photons per fluorescein molecule are detected.

E. Determination of the Number of Molecules Per Unit Area

Aminopropylated glass microscope slides prepared according to the methods discussed above were utilized in order to establish the density of labeling of the slides. The free amino termini of the slides were reacted with FITC (fluorescein isothiocyanate) which forms a covalent linkage with the amino group. The slide is then scanned to count the number of fluorescent photons generated in a region which, using the estimated 40–50 photons per fluorescent molecule, enables the calculation of the number of molecules which are on the surface per unit area.

A slide with aminopropyl silane on its surface was immersed in a 1 mM solution of FITC in DMF for 1 hour at about ambient temperature. After reaction, the slide was washed twice with DMF and then washed with ethanol, water, and then ethanol again. It was then dried and stored in the dark until it was ready to be examined.

Through the use of curves similar to those shown in FIGS. 11A and 11B, and by integrating the fluorescent counts under the exponentially decaying signal, the number of free amino groups on the surface after derivatization was determined. It was determined that slides with labeling densities of 1 fluorescein per $10^3 \times 10^3$ to ~2×2 nm could be reproducibly made as the concentration of aminopropyltriethoxysilane varied from $10^{-5}\%$ to $10^{-1}\%$.

F. Removal of NVOC and Attachment of A Fluorescent Marker

NVOC-GABA groups were attached as described above. The entire surface of one slide was exposed to light so as to expose a free amino group at the end of the gamma amino butyric acid. This slide, and a duplicate which was not exposed, were then exposed to fluorescein isothiocyanate (FITC).

FIG. 12A illustrates the slide which was not exposed to light, but which was exposed to FITC. The units of the x axis are time and the units of the y axis are counts. The trace contains a certain amount of background fluorescence. The duplicate slide was exposed to 350 nm broadband illumination for about 1 minute (12 mW/cm$^2$, ~350 nm illumination), washed and reacted with FITC. The fluorescence curves for this slide are shown in FIG. 12B. A large increase in the level of fluorescence is observed, which indicates photolysis has exposed a number of amino groups on the surface of the slides for attachment of a fluorescent marker.

G. Use of a Mask in Removal of NVOC

The next experiment was performed with a 0.1% aminopropylated slide. Light from a Hg-Xe arc lamp was imaged onto the substrate through a laser-ablated chrome-on-glass mask in direct contact with the substrate.

This slide was illuminated for approximately 5 minutes, with 12 mW of 350 nm broadband light and then reacted with the 1 mM FITC solution. It was put on the laser detection scanning stage and a graph was plotted as a two-dimensional representation of position color-coded for fluorescence intensity. The fluorescence intensity (in counts) as a function of location is given on the color scale to the right of FIG. 13A for a mask having 100×100 $\mu$m squares.

The experiment was repeated a number of times through various masks. The fluorescence pattern for a 50 $\mu$m mask is illustrated in FIG. 13B, for a 20 $\mu$m mask in FIG. 13C, and for a 10 $\mu$m mask in FIG. 13D. The mask pattern is distinct down to at least about 10 $\mu$m squares using this lithographic technique.

H. Attachment of YGGFL and Subsequent Exposure to Herz Antibody and Goat Antimouse In order to establish that receptors to a particular polypeptide sequence would bind to a surface-bound peptide and be detected, Leu enkephalin was coupled to the surface and recognized by an antibody. A slide was derivatized with 0.1% amino propyl-triethoxysilane and protected with NVOC. A 500 $\mu$m checkerboard mask was used to expose the slide in a flow cell using backside contact printing. The Leu enkephalin sequence ($H_2$N-tyrosine,glycine,glycine, phenylalanine,leucine-CO$_2$H, otherwise referred to herein as YGGFL) was attached via its carboxy end to the exposed amino groups on the surface of the slide. The peptide was added in DMF solution with the BOP/HOBT/DIEA coupling reagents and recirculated through the flow cell for 2 hours at room temperature.

A first antibody, known as the Herz antibody, was applied to the surface of the slide for 45 minutes at 2 μg/ml in a supercocktail (containing 1% BSA and 1% ovalbumin also in this case). A second antibody, goat anti-mouse fluorescein conjugate, was then added at 2 μg/ml in the supercocktail buffer, and allowed to incubate for 2 hours.

An image taken at sum steps indicated that not only can deprotection be carried out in a well defined pattern, but also that (1) the method provides for successful coupling of peptides to the surface of the substrate, (2) the surface of a bound peptide is available for binding with an antibody, and (3) that the detection apparatus capabilities are sufficient to detect binding of a receptor.

I. Monomer-by-Monomer Formation of YGGFL and Subsequent Exposure to Labeled Antibody Monomer-by-monomer synthesis of YGGFL and GGFL in alternate squares was performed on a slide in a checkerboard pattern and the resulting slide was exposed to the Herz antibody. This experiment and the results thereof are illustrated in FIGS. 14A, 14B, 15A, and 15B.

In FIG. 14A, a slide is shown which is derivatized with the aminopropyl group, protected in this case with t-BOC (t-butoxycarbonyl). The slide was treated with TFA to remove the t-BOC protecting group. E-aminocaproic acid, which was t-BOC protected at its amino group, was then coupled onto the aminopropyl groups. The aminocaproic acid serves as a spacer between the aminopropyl group and the peptide to be synthesized. The amino end of the spacer was deprotected and coupled to NVOC-leucine. The entire slide was then illuminated with 12 mW of 325 nm broadband illumination. The slide was then coupled with NVOC-phenylalanine and washed. The entire slide was again illuminated, then coupled to NVOC-glycine and washed. The slide was again illuminated and coupled to NVOC-glycine to form the sequence shown in the last portion of FIG. 14A.

As shown in FIG. 14B, alternating regions of the slide were then illuminated using a projection print using a 500×500 μm checkerboard mask; thus, the amino group of glycine was exposed only in the lighted areas. When the next coupling chemistry step was carried out, NVOC-tyrosine was added, and it coupled only at those spots which had received illumination. The entire slide was then illuminated to remove all the NVOC groups, leaving a checkerboard of YGGFL in the lighted areas and in the other areas, GGFL. The Herz antibody (which recognizes the YGGFL, but not GGFL) was then added, followed by goat anti-mouse fluorescein conjugate.

The resulting fluorescence scan is shown in FIG. 15A, and the color coding for the fluorescence intensity is again given on the right. Dark areas contain the tetrapeptide GGFL, which is not recognized by the Herz antibody (and thus there is no binding of the goat anti-mouse antibody with fluorescein conjugate), and in the red areas YGGFL is present. The YGGFL pentapeptide is recognized by the Herz antibody and, therefore, there is antibody in the lighted regions for the fluorescein-conjugated goat anti-mouse to recognize.

Similar patterns are shown for a 50 μm mask used in direct contact ("proximity print") with the substrate in FIG. 15B. Note that the pattern is more distinct and the corners of the checkerboard pattern are touching when the mask is placed in direct contact with the substrate (which reflects the increase in resolution using this technique).

J. Monomer-by-Monomer Synthesis of YGGFL and PGGFL

A synthesis using a 50 μm checkerboard mask similar to that shown in FIG. 15B was conducted. However, P was added to the GGFL sites on the substrate through an additional coupling step. P was added by exposing protected GGFL to light, and subsequence exposure to P in the manner set forth above. Therefore, half of the regions on the substrate contained YGGFL and the remaining half contained PGGFL.

The fluorescence plot for this experiment is provided in FIG. 16. As shown, the regions are again readily discernable. This experiment demonstrates that antibodies are able to recognize a specific sequence and that the recognition is not length-dependent.

K. Monomer-by-Monomer Synthesis of YGGFL and YPGGFL

In order to further demonstrate the operability of the invention, a 50 μm checkerboard pattern of alternating YGGFL and YPGGFL was synthesized on a substrate using techniques like those set forth above. The resulting fluorescence plot is provided in FIG. 17. Again, it is seen that the antibody is clearly able to recognize the YGGFL sequence and does not bind significantly at the YPGGFL regions.

L. Synthesis of an Array of Sixteen Different Amino Acid Sequences and Estimation of Relative Binding Affinity to Herz Antibody Using techniques similar to those set forth above, an array of 16 different amino acid sequences (replicated four times) was synthesized on each of two glass substrates. The sequences were synthesized by attaching the sequence NVOC-GFL across the entire surface of the slides. Using a series of masks, two layers of amino acids were then selectively applied to the substrate. Each region had dimensions of 0.25 cm×0.0625 cm. The first slide contained amino acid sequences containing only L amino acids while the second slide contained selected D amino acids. FIGS. 18A and 18B illustrate a map of the various regions on the first and second slides, respectively. The patterns shown in FIGS. 18A and 18B were duplicated four times on each slide. The slides were then exposed to the Herz antibody and fluorescein-labeled goat anti-mouse.

FIG. 19 is a fluorescence plot of the first slide, which contained only L amino acids. Red indicates strong binding (149,000 counts or more) while black indicates little or no binding of the Herz antibody (20,000 counts or less). The bottom right-hand portion of the slide appears "cut off" because the slide was broken during processing. The sequence YGGFL is clearly most strongly recognized. The sequences YAGFL and YSGFL also exhibit strong recognition of the antibody. By contrast, most of the remaining sequences show little or no binding. The four duplicate portions of the slide are extremely consistent in the amount of binding shown therein.

FIG. 20 is a fluorescence plot of the second slide. Again, strongest binding is exhibited by the YGGFL sequence. Significant binding is also detected to YaGFL, YsGFL, and YpGFL (where L-amino acids are identified by one upper case letter abbreviation, and D-amino acids are identified by one lower case letter abbreviation). The remaining sequences show less binding with the antibody. Note the low binding efficiency of the sequence yGGFL.

Table 6 lists the various sequences tested in order of relative fluorescence, which provides information regarding relative binding affinity.

TABLE 6

Apparent Binding to Herz Ab

| L-a.a. Set | D-a.a. Set |
|---|---|
| YGGFL | YGGFL |
| YAGFL | YaGFL |
| YSGFL | YsGFL |
| LGGFL | YpGFL |
| FGGFL | fGGFL |
| YPGFL | yGGFL |
| LAGFL | faGFL |
| FAGFL | wGGFL |
| WGGFL | yaGFL |
|  | fpGFL |
|  | waGFL |

VIII. ILLUSTRATIVE ALTERNATIVE EMBODIMENT

According to an alternative embodiment of the invention, the methods provide for attaching to the surface a caged binding member which in its caged form has a relatively low affinity for other potentially binding species, such as receptors and specific binding substances.

According to this alternative embodiment, the invention provides methods for forming predefined regions on a surface of a solid support, wherein the predefined regions are capable of immobilizing receptors. The methods make use of caged binding members attached to the surface to enable selective activation of the predefined regions. The caged binding members are liberated to act as binding members ultimately capable of binding receptors upon selective activation of the predefined regions. The activated binding members are then used to immobilize specific molecules such as receptors on the predefined region of the surface. The above procedure is repeated at the same or different sites on the surface so as to provide a surface prepared with a plurality of regions on the surface containing, for example, the same or different receptors. When receptors immobilized in this way have a differential affinity for one or more ligands, screenings and assays for the ligands can be conducted in the regions of the surface containing the receptors.

The alternative embodiment may make use of novel caged binding members attached to the substrate. Caged (unactivated) members have a relatively low affinity for receptors of substances that specifically bind to uncaged binding members when compared with the corresponding affinities of activated binding members. Thus, the binding members are protected from reaction until a suitable source of energy is applied to the regions of the surface desired to be activated. Upon application of a suitable energy source, the caging groups labilize, thereby presenting the activated binding member. A typical energy source will be light.

Once the binding members on the surface are activated they may be attached to a receptor. The receptor chosen may be a monoclonal antibody, a nucleic acid sequence, a drug receptor, etc. The receptor will usually, though not always, be prepared so as to permit attaching it, directly or indirectly, to a binding member. For example, a specific binding substance having a strong binding affinity for the binding member and a strong affinity for the receptor or a conjugate of the receptor may be used to act as a bridge between binding members and receptors if desired. The method uses a receptor prepared such that the receptor retains its activity toward a particular ligand.

Preferably, the caged binding member attached to the solid substrate will be a photoactivatable biotin complex, i.e., a biotin molecule that has been chemically modified with photoactivatable protecting groups so that it has a significantly reduced binding affinity for avidin or avidin analogs than does natural biotin. In a preferred embodiment, the protecting groups localized in a predefined region of the surface will be removed upon application of a suitable source of radiation to give binding members, that are biotin or a functionally analogous compound having substantially the same binding affinity for avidin or avidin analogs as does biotin.

In another preferred embodiment, avidin or an avidin analog is incubated with activated binding members on the surface until the avidin binds strongly to the binding members. The avidin so immobilized on predefined regions of the surface can then be incubated with a desired receptor or conjugate of a desired receptor. The receptor will preferably be biotinylated, e.g., a biotinylated antibody, when avidin is immobilized on the predefined regions of the surface. Alternatively, a preferred embodiment will present an avidin/biotinylated receptor complex, which has been previously prepared, to activated binding members on the surface.

IX. CONCLUSION

The present inventions provide greatly improved methods and apparatus for synthesis of polymers on substrates. It is to be understood that the above description is intended to be illustrative and not restrictive. Many embodiments will be apparent to those of skill in the art upon reviewing the above description. By way of example, the invention has been described primarily with reference to the use of photoremovable protective groups, but it will be readily recognized by those of skill in the art that sources of radiation other than light could also be used. For example, in some embodiments it may be desirable to use protective groups which are sensitive to electron beam irradiation, x-ray irradiation, in combination with electron beam lithograph, or x-ray lithography techniques. Alternatively, the group could be removed by exposure to an electric current. The scope of the invention should, therefore, be determined not with reference to the above description, but should instead be determined with reference to the appended claims, along with the full scope of equivalents to which such claims are entitled.

What is claimed is:

1. An apparatus for detection of fluorescent marked locations on a substrate comprising:
    a) a substrate that comprises a plurality of different polymer sequences coupled to a surface of said substrate, wherein said plurality of different polymer sequences comprises a plurality of different oligonucleotide sequences, each of said different polymer sequences being coupled in a different known location of said surface, each of said known locations having an area of $10^{-2}$ $cm^2$ or less;
    b) a light source for directing light at said surface of said substrate;
    c) a detector for detecting light fluoresced from said surface in response to said light source;
    d) a translator for translating said substrate relative to said light source whereby a plurality of said known locations of said surface of said substrate are exposed to said light; and
    e) a data storage system for storing fluoresced light intensity as a function of location on said surface, said data storage system coupled to said translator and said detector.

2. The apparatus as recited in claim 1, wherein said plurality of different oligonucleotide sequences comprises greater than 10 different oligonucleotide sequences on said surface of said substrate.

3. The apparatus as recited in claim 1, wherein said plurality of different oligonucleotide sequences comprises at least 100 different oligonucleotide sequences on on said surface of said substrate.

4. The apparatus as recited in claim 1, wherein said plurality of different oligonucleotide sequences comprises at least 1000 different oligonucleotide sequences on said surface of said substrate.

5. The apparatus as recited in claim 1, wherein said plurality of different oligonucleotide sequences comprises greater than 10,000 different oligonucleotide sequences on said surface of said substrate.

6. The apparatus as recited in claim 1, wherein said plurality of different oligonucleotide sequences comprises greater than 100,000 different oligonucleotide sequences on said surface of said substrate.

7. The apparatus as recited in claim 1, wherein each of said different oligonucleotide sequences is in a known location on said surface of said substrate has an area of less than 10,000 $\mu m^2$.

8. An apparatus for detecting fluorescent marked locations on a surface of a substrate, comprising:

a point light source for generating an excitation light;

a substrate that comprises a plurality of different polymers coupled to a surface of said substrate, wherein said plurality of different polymers comprises a plurality of different oligonucleotide sequences, each of said different polymer sequences being coupled in a different known location of said surface, each of said known locations having an area of $10^{-2}$ cm$^2$ or less;

an objective lens for focusing said point light source at said surface of said substrate, whereby said fluorescently marked locations emit a fluoresced light in response to said excitation light;

an x-y translation stage for moving said substrate relative to said excitation light;

a dichroic mirror for reflecting light having a wavelength of said excitation light and passing light having a wavelength of said fluoresced light;

a photomultiplier and photon counter for detecting said fluoresced light; and an appropriately programmed computer for recording said fluoresced light as a function of a position on said surface of said substrate from which said fluoresced light was emitted.

9. The apparatus as recited in claim 8, wherein said plurality of different oligonucleotide sequences comprises greater than 10 different oligonucleotide sequences on said surface of said substrate.

10. The apparatus as recited in claim 8, wherein said plurality of different oligonucleotide sequences comprises at least 100 different oligonucleotide sequences on said surface of said substrate.

11. The apparatus as recited in claim 8, wherein said plurality of different oligonucleotide sequences comprises at least 1000 different oligonucleotide sequences on said surface of said substrate.

12. The apparatus as recited in claim 8, wherein said plurality of different oligonucleotide sequences comprises greater than 10,000 different oligonucleotide sequences on said surface of said substrate.

13. The apparatus as recited in claim 8, wherein said plurality of different oligonucleotide sequences comprises greater than 100,000 different oligonucleotide sequences on said surface of said substrate.

14. The apparatus as recited in claim 8, wherein each of said different oligonucleotide sequences is in a known location on said surface of said substrate having an area of less than 10,000 $\mu m^2$.

15. A method of detecting the presence of a fluorescent marker on a surface of a substrate, the method comprising:

directing an excitation light at the surface of the substrate; and detecting light fluoresced from the surface of the substrate at a plurality of locations on said substrate, wherein said surface of said substrate comprises a plurality of different oligonucleotides covalently bound thereto, each of said different oligonucleotides being bound at a different known location on the substrate, and said fluorescent marker comprises a fluorescently labeled target nucleic acid that is capable of hybridizing with one or more of said plurality of different oligonucleotides.

16. A method of determining whether a fluorescently labeled ligand binds to one or more of a plurality of different polymer sequences, wherein said fluorescently labeled ligand comprises a fluorescently labeled target nucleic acid, and said plurality of different polymer sequences on surface of a substrate comprises a plurality of different oligonucleotides, comprising:

providing a plurality of different polymer sequences covalently bound to a surface of a substrate, each of said different polymer sequences being bound at a known location on the surface of the substrate;

contacting the surface of the substrate with the fluorescently labeled ligand;

washing the surface to remove unbound fluorescently labeled ligand from the surface of the substrate; and detecting binding between the fluorescently labeled ligand and different polymer sequences, said detecting step comprising directing an excitation light at the surface of the substrate, and detecting light fluoresced from the surface of the substrate at a plurality of locations on said surface of said substrate.

17. The method as recited in claim 16, wherein the plurality of different polymer sequences comprises greater than 10 different oligonucleotides on said surface of said substrate.

18. The method as recited in claim 16, wherein the plurality of different polymer sequences comprises at least 100 different oligonucleotides on said surface of said substrate.

19. The method as recited in claim 16, wherein the plurality of different polymer sequences comprises at least 1000 different oligonucleotides on said surface of said substrate.

20. The method as recited in claim 16, wherein the plurality of different polymer sequences comprises greater than 10,000 different oligonucleotides on said surface of said substrate.

21. The method as recited in claim 16, wherein the plurality of different polymer sequences comprises greater than 100,000 different oligonucleotides on said surface of said substrate.

22. The method as recited in claim 16, wherein each of the different polymer sequences is in a known location on said surface of said substrate having an area of less than 10,000 $\mu m^2$.

23. A polynucleotide analysis apparatus comprising:

a substrate that comprises a plurality of different polynucleotides, each of said different polynucleotides being coupled in a different known location of a surface of said substrate, each of said known locations having an area of $10^{-2}$ cm$^2$ or less, said substrate comprising more than 10 of such polynucleotides, at least some of said polynucleotides coupled to labeled target molecules; a light source for directing light at said surface of said substrate; a detector for detecting light fluoresced from said surface in response to said light source; a translator for translating said substrate relative to said light source whereby a plurality of said known locations of said substrate are exposed to light; and a data storage system for storing fluoresced light intensity as a function of location on said substrate, said data storage system coupled to said translator and said detector, said data storage system storing light intensity as a function of location on said surface of said substrate.

24. A method of determining whether a fluorescently labeled ligand binds to one or more of a plurality of different polymer sequences, wherein said fluorescently labeled ligand comprises a fluorescently labeled target nucleic acid, said plurality of different polymer sequences a surface of a substrate and comprise a plurality of different polynucleotides, comprising:

providing at least 1000 different polymer sequences bound to said surface of said substrate, each of said different polymer sequences being bound at a known location on the surface of the substrate, said polymer sequences comprising polynucleotides;

contacting the surface of the substrate with the fluorescently labeled ligand;

washing the surface to remove unbound fluorescently labeled ligand from the surface of the substrate; and detecting binding between the fluorescently labeled ligand and at least some of the more than 1000 different polymer sequences, said detecting step comprising directing an excitation light at the surface of the substrate, and detecting light fluoresced from the surface of the substrate at a plurality of locations on said surface of said substrate.

25. The method as recited in claim 16, wherein the plurality of different polymer sequences comprises greater than 10 different polynucleotides on said surface of said substrate.

26. The method as recited in claim 16, wherein the plurality of different polymer sequences comprises at least 100 different polynucleotides on said surface of said substrate.

27. The method as recited in claim 16, wherein the plurality of different polymer sequences comprises at least 1000 different polynucleotides on said surface of said substrate.

28. The method as recited in claim 16, wherein the plurality of different polymer sequences comprises greater than 10,000 different polynucleotides on said surface of said substrate.

29. The method as recited in claim 16, wherein the plurality of different polymer sequences comprises greater than 100,000 different polynucleotides on said surface of said substrate.

30. The method as recited in claim 16, wherein each of the different polymer sequences is in a known location on a surface of said substrate having an area of less than 10,000 $\mu$m$^2$.

31. An apparatus for detecting labeled comprising:

(a) a substrate having a surface comprising at least 10 different nucleic acids at known locations on the surface of the substrate, each of the known locations having an area of $10^{-2}$ cm$^2$ or less, some of the nucleic acids being bound to labeled receptors;

(b) an excitation light source;

(c) a detector adapted to receive a signal from said bound labeled receptors on said surface;

(d) a translator adapted to move said substrate relative to said detector; and (e) a data collection system adapted to receive input from said detector.

32. The apparatus of claim 31 wherein the surface of the substrate has at least 100 different nucleic acids.

33. The apparatus of claim 31 wherein the surface of the substrate has at least 1,000 different nucleic acids.

34. The apparatus of claim 31 wherein the surface of the substrate has at least 10,000 different nucleic acids.

35. The apparatus of claim 31 wherein the surface of the substrate has at least 400 different nucleic acids/cm$^2$.

36. The apparatus of claim 31 wherein the surface of the substrate has at least 1,000 different nucleic acids/cm$^2$.

* * * * *

UNITED STATES PATENT AND TRADEMARK OFFICE
CERTIFICATE OF CORRECTION

PATENT NO. : 6,225,625 B1
DATED : May 1, 2001
INVENTOR(S) : Michael C. Pirrung et al.

It is certified that error appears in the above-identified patent and that said Letters Patent is hereby corrected as shown below:

Column 33,
Lines 22-44,
24. A method of determining whether a fluorescently labeled ligand binds to one or more of a plurality of different polymer sequences, wherein said fluorescently labeled ligand comprises a fluorescently labeled target nucleic acid, and said plurality of different polymer sequences are bound to a surface of a substrate and comprise a plurality of different polynucleotide, comprising:

providing at least 1000 different polymer sequences bound to said surface of said substrate, each of said different polymer sequences being bound at a known location on the surface of the substrate, said polymer sequences comprising polynucleotides;

contacting the surface of the substrate with the fluorescently labeled ligand;

washing the surface to remove unbound fluorescently labeled ligand from the surface of the substrate; and detecting binding between the fluorescently labeled ligand and at least some of the more than 1000 different polymer sequences, said detecting step comprising directing an excitation light at the surface of the substrate, and detecting light fluoresced from the surface of the substrate at a plurality of locations on said surface of said substrate.

Column 34,
Lines 22-36,
31. An apparatus for detecting labeled nucleic acids comprising:

(a) a substrate having a surface comprising at least 10 different nucleic acids at known locations on the surface of the substrate, each of the known locations having an area of $10^{-2}$ cm$^2$ or less, some of the nucleic acids being bound to labeled [receptors] nucleic acids;

UNITED STATES PATENT AND TRADEMARK OFFICE
CERTIFICATE OF CORRECTION

PATENT NO. : 6,225,625 B1
DATED : May 1, 2001
INVENTOR(S) : Michael C. Pirrung et al.

It is certified that error appears in the above-identified patent and that said Letters Patent is hereby corrected as shown below:

(b) an excitation light source;
    (c) a detector adapted to receive a signal from said bound labeled [receptors] <u>nucleic acids</u> on said surface;
    (d) a translator adapted to move said substrate relative to said detector; and
    (e) a data collection system adapted to receive input from said detector.

Signed and Sealed this

Thirtieth Day of April, 2002

*Attest:*

JAMES E. ROGAN
*Attesting Officer*     *Director of the United States Patent and Trademark Office*